(12) United States Patent
Abu Khabar

(10) Patent No.: US 11,648,251 B2
(45) Date of Patent: May 16, 2023

(54) TTP PHOSPHORYLATION AS A BIOMARKER IN TARGETED THERAPY

(71) Applicant: KING FAISAL SPECIALIST HOSPITAL & RESEARCH CENTRE, Riyadh (SA)

(72) Inventor: Khalid S. Abu Khabar, Riyadh (SA)

(73) Assignee: KING FAISAL SPECIALIST HOSPITAL & RESEARCH CENTRE, Riyadh (SA)

(*) Notice: Subject to any disclaimer, the term of this patent is extended or adjusted under 35 U.S.C. 154(b) by 555 days.

(21) Appl. No.: 16/710,455

(22) Filed: Dec. 11, 2019

(65) Prior Publication Data

US 2021/0177852 A1 Jun. 17, 2021

(51) Int. Cl.
| | | |
|---|---|---|
| *A61K 31/517* | (2006.01) | |
| *A61K 31/519* | (2006.01) | |
| *A61P 35/00* | (2006.01) | |
| *A61K 45/06* | (2006.01) | |
| *G01N 33/50* | (2006.01) | |
| *G01N 33/574* | (2006.01) | |
| *G01N 33/68* | (2006.01) | |

(52) U.S. Cl.
CPC .......... *A61K 31/519* (2013.01); *A61K 31/517* (2013.01); *A61K 45/06* (2013.01); *A61P 35/00* (2018.01); *G01N 33/5011* (2013.01); *G01N 33/57484* (2013.01); *G01N 33/6893* (2013.01); *G01N 2800/52* (2013.01)

(58) Field of Classification Search
CPC ......... G01N 33/57484; G01N 2800/52; A61K 31/517; A61K 31/519
USPC ...................... 435/7.23; 436/519; 514/249
See application file for complete search history.

(56) References Cited

U.S. PATENT DOCUMENTS

| | | | |
|---|---|---|---|
| 8,962,267 B1* | 2/2015 | De Wijn ............... | C12Q 1/485 506/10 |
| 10,961,587 B2* | 3/2021 | Tajbakhsh ............ | C12Q 1/6886 |
| 2020/0232043 A1* | 7/2020 | Ruijtenbeek ......... | C12Q 1/6886 |
| 2022/0112565 A1* | 4/2022 | Stone ................... | C12Q 1/6886 |

* cited by examiner

*Primary Examiner* — Raymond J Henley, III
(74) *Attorney, Agent, or Firm* — Saliwanchik, Lloyd & Eisenschenk

(57) ABSTRACT

The present invention relates to a method of determining if a patient is likely to respond to a treatment with a targeted therapy compound selected from protein kinase inhibitors, small molecule inhibitors, and monoclonal antibody-based compounds. The present invention further relates to a method of identifying a targeted therapy compound selected from protein kinase inhibitors, small molecule inhibitors, and monoclonal antibody-based compounds for personalized medicine. The present invention also relates to a method of treatment of cancer in a patient. The present invention also relates to a targeted therapy compound selected from protein kinase inhibitors, small molecule inhibitors, and monoclonal antibody-based compounds for use in a method of treatment of cancer in a patient.

13 Claims, 6 Drawing Sheets

Specification includes a Sequence Listing.

TTP PHOSPHORYLATION AS A BIOMARKER IN TARGETED THERAPY

The Sequence Listing for this application is labeled "SeqList-10Dec19-ST25.txt", which was created on Dec. 10, 2019 and is 4 KB. The entire content is incorporated herein by reference in its entirety.

FIELD OF THE INVENTION

The present invention relates to a method of determining if a patient is likely to respond to a treatment with a targeted therapy compound selected from protein kinase inhibitors, small molecule inhibitors, and monoclonal antibody-based compounds. The present invention further relates to a method of identifying a targeted therapy compound selected from protein kinase inhibitors, small molecule inhibitors, and monoclonal antibody-based compounds for personalized medicine. The present invention also relates to a method of treatment of cancer in a patient. The present invention also relates to a targeted therapy compound selected from protein kinase inhibitors, small molecule inhibitors, and monoclonal antibody-based compounds for use in a method of treatment of cancer in a patient.

BACKGROUND OF THE INVENTION

A key RNA-binding protein that promotes AU-rich mRNA deadenylation and decay is the zinc finger protein, tristetraprolin (TTP/ZFP36). Many human tumors are found to be associated with deficiency of TTP, which is linked to hallmarks of cancer. The aberrant expression or activity of TTP/ZFP36 could be attributed to changes at different levels of regulation, including transcriptional (e.g. epigenetic), post-transcriptional, and post-translational regulation.

Phosphorylation of TTP/ZFP36 by various protein kinases is one of the posttranslational modifications that profoundly affect its cellular localization and activity [1], [2], [3]. For example, the p38/MK2 is a pathway that leads to TTP phosphorylation preventing its ability to recruit mRNA decay machinery and subsequently leading to overproduction of ARE-mRNA products.

Protein phosphorylation and dephosphorylation events are mediated through the action of protein kinases. Protein phosphorylation by kinases is a post-translational mechanism that affects numerous cellular responses to stimuli and influences downstream transcriptional and post-transcriptional events. Human cells contain hundreds of kinases, many of which can be aberrantly active in cancer cells. Kinase activity can cause abnormal regulation of gene expression at different levels.

Phosphorylation of proteins by different protein kinases is a mechanism of post-translational modification that highly affects the cellular localization and activity of the proteins. Protein phosphorylation results in alteration of protein structure and conformation, and modifies its activity and function. The commonly phosphorylated amino acids in eukaryotes are serine, threonine, and tyrosine. The phosphorylation is mediated through the action of a protein kinase (PK), and can be reverse through the action of a phosphatase. Nearly 2% of the human genome encode for PKs, representing about 538 genes which are subdivided into typical, or conventional, and atypical protein kinases, according to the kinase database (http://kinase.com/kinbase/). The majority of typical PKs phosphorylates serine/threonine (STPKs) and only a minority of PKs phosphorylates tyrosine, and atypical PKs are mostly STPKs. To date, FDA has approved 37 small molecule kinase inhibitors and many others are in phase-2/3 clinical trials. Most of the approved kinase drugs are intended for treatment of cancers, and only few of them have been approved for treatment of non-cancerous conditions, such as sirolimus for organ rejection.

Previous reports indicate that phosphorylation events during inflammation lead to stabilization of TTP/ZFP36 and that de-phosphorylated TTP is unstable and less abundant in cells [1],[2]. Unlike the active unphosphorylated TTP/ZFP36, MK2-phosphorylated TTP is of increased abundance due to protein stabilization, and is less active.

It has been shown that TTP/ZFP36 has multiple phosphorylation sites, and thus can be affected by several signaling pathways and many kinases [4]. For example, major MK2 sites for TTP/ZFP36 phosphorylation are mouse/human serine 52/60 and 178/186. However, there are many other potential amino acid sites for phosphorylation and for a variety of kinase targets.

Due to high occurrence of side effects associated with various drugs, it is important to assess, prior to an administration of a drug, whether a treatment with a certain drug is likely to be successful. Personalized medicine allows for customizing the specific treatment to a patient's needs, i.e. the patient's genetic and phenotypical features, and thus allows for targeted therapy of a patient. There is an urgent need for suitable biomarkers for assessing whether a patient is likely to respond to a drug. For example, there is the urgent need for biomarkers that are capable of indicating whether a targeted therapy compound selected from protein kinase inhibitors, small molecule inhibitors, and monoclonal antibody-based compounds effectively evokes a therapeutic effect. The present invention thus aims at providing a universal biomarker for determining whether a patient is likely to respond to a treatment, and for selecting an appropriate drug for a patient. The present invention further aims at providing a method of treatment of cancer, and a targeted therapy compound selected from protein kinase inhibitors, small molecule inhibitors, and monoclonal antibody-based compounds for use in a method of treatment of cancer.

SUMMARY OF THE INVENTION

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

In a first aspect, the present invention relates to a method of determining if a patient is likely to respond to a treatment with a targeted therapy compound selected from protein kinase inhibitors, small molecule inhibitors, and monoclonal antibody-based compounds, wherein the method comprises the following steps:

i) providing a tumor sample of a patient, wherein said tumor sample comprises cancerous tissue and/or cancerous cells, ii) determining a level of phosphorylated tristetraprolin (TTP) in said tumor sample, and
iii) comparing the level of phosphorylated TTP determined in step ii) to a control, wherein said control is preferably a reference value and/or a reference sample, wherein an increased level of phosphorylated TTP in said tumor sample compared to said control indicates that said patient is likely to respond to a treatment using a targeted therapy compound.

In one embodiment, said method further comprises
providing a tumor sample of said patient, and treating said tumor sample with one or more targeted therapy compound(s),
determining a level of phosphorylated TP in said treated tumor sample, and,
comparing the level of phosphorylated TP determined in said treated tumor sample to the level of phosphorylated TTP determined in step ii),
wherein a decreased level of phosphorylated TTP in said treated tumor sample compared to the level of phosphorylated TTP determined in step ii) indicates that said patient is likely to respond to a treatment with said one or more targeted therapy compound(s).

In one embodiment, said determining of a level of phosphorylated TTP is performed using an antibody or antigen-binding fragment thereof targeting phosphorylated TTP and/or TTP.

In one embodiment, said step ii) further comprises determining a cancer-related genetic variation in said tumor sample, such as a KRAS mutation and/or an EGFR amplification.

In a further aspect, the present invention further relates to a method of identifying a targeted therapy compound selected from protein kinase inhibitors, small molecule inhibitors, and monoclonal antibody-based compounds for personalized medicine, preferably precision cancer therapy of a cancer patient, comprising, in any order, the following steps:
  a. obtaining a tumor sample from a patient,
  b. optionally, determining a level of phosphorylated TTP in said tumor sample,
  c. providing one or more targeted therapy compound(s) to be tested,
  d. treating said tumor sample with said one or more targeted therapy compound(s),
  e. determining whether said one or more targeted therapy compound(s) reduce(s) the levels of phosphorylated TTP in said treated sample compared to a control, wherein a reduction in the level of phosphorylated TTP indicates that said one or more targeted therapy compound (s) is/are effective for treating said patient.

In one embodiment, said control in step e) is a level of phosphorylated TTP determined in step b), and/or is a reference value, and/or is a level of phosphorylated TTP determined in a reference sample.

In one embodiment, said reduction is a reduction by at least 15%, preferably by at least 20%, more preferably by at least 25%.

In one embodiment, said level of phosphorylated TTP is determined using an antibody or antigen-binding fragment thereof targeting phosphorylated TTP.

In one embodiment, the precision cancer therapy is a pan-cancer precision cancer therapy capable of treating a cancer regardless of the tissue type or subtype or molecular sub-type of the cancer including solid tumors, hematological tumors, leukemias, lymphomas, organ-specific tumors such as breast, colon, prostate, liver, and metastatic tumors of any origin, including subtypes such as hormone positive, hormone negative, Microsatellite Instability high or low, KRAS mutant, p53 mutant cancer, and cancers with amplified genes.

In a further aspect, the present invention further relates to a method of treatment of cancer in a patient, wherein said cancer is characterized by an increased level of phosphorylated TTP in cancer cells compared to non-cancerous cells, wherein said method comprises administering an effective dose of a targeted therapy compound selected from protein kinase inhibitors, small molecule inhibitors, and monoclonal antibody-based compounds to a patient in need thereof having said cancer.

In one embodiment, said method comprises the steps of:
  a. obtaining a tumor sample, and optionally a non-tumor control sample, from the patient,
  b. determining the level of phosphorylated TTP in said tumor sample, and optionally in said non-tumor control sample,
  c. administering a therapeutically effective amount of said targeted therapy compound, if there is an increased level of phosphorylated TTP in the tumor sample compared to a control, which is optionally the non-tumor control sample of said patient, as determined in step b).

In one embodiment, said targeted therapy compound is selected from BI-3406, lapitinib, AZ628, sorafenib2, TAK-6323, regorafenib4, CEP-32496, cabozantinib, and polo-like kinase inhibitors including PCM-075, volasertib, BI 2536, rigosertib (ON 01910), HMN-214, GSK461364, R03280, NMS-P937, TAK-960, cyclapolin 1, DAP-81, ZK-thiazolidinone, compound 36 (imidazopyridine derivative), LFM-A13, poloxin (thymoquinone derivative), poloxipan, purpurogallin (benzotropolone-containing compound), MLN0905, and SBE13, preferably volasertib and lapitinib.

In one embodiment, said targeted therapy compound is co-administered with a chemotherapeutic agent, and/or with a therapeutic monoclonal antibody or antigen-binding fragment thereof, and/or with a checkpoint inhibitor including CTLA-4, PD-1, and PD-L1 targeting agents, and/or with an interferon selected from Type-I IFN, Type-II IFN and Type-III IFN, and/or with a cytokine inhibitor, and/or with a small molecule drug.

In one embodiment, the level of phosphorylated TTP is reduced by administering said targeted therapy compound.

In one embodiment, said reduction is a reduction by at least 15%, preferably by at least 20%, more preferably by at least 25%.

In one embodiment, the method of treatment of cancer in a patient comprises, prior to said administering, a method of determining if a patient is likely to respond to a treatment as defined in any of the embodiments above and/or a method of identifying a targeted therapy compound for personalized medicine as defined in any of the embodiments above.

In one embodiment, the method further comprises monitoring a treatment response, comprising the following steps:
  i) obtaining a sample from said patient of a first time point and a second time point,
  ii) determining a level of phosphorylated TTP in said first sample of said first time point and in said second sample of said second time point,
  iii) comparing the level determined in said first sample to the level determined in said second sample, wherein a decrease in the level determined in the second sample compared to the level determined in the first sample indicates that said targeted therapy compound is effective in treating said cancer.

In a further aspect, the present invention further relates to a targeted therapy compound selected from protein kinase inhibitors, small molecule inhibitors, and monoclonal antibody-based compounds for use in a method of treatment of cancer in a patient, wherein said cancer is characterized by an increased level of phosphorylated TTP in cancer cells compared to non-cancerous cells, wherein said method comprises administering an effective dose of said targeted therapy compound to a patient in need thereof having said cancer.

In one embodiment, said method comprises the steps of:
a. obtaining a tumor sample, and optionally a non-tumor control sample, from the patient,
b. determining the level of phosphorylated TP in said tumor sample, and optionally in said non-tumor control sample,
c. administering a therapeutically effective amount of said targeted therapy compound, if there is an increased level of phosphorylated TTP in the tumor sample compared to a control, which is optionally the non-tumor control sample of said patient, as determined in step b).

In one embodiment, said targeted therapy compound is selected from BI-3406, lapitinib, AZ628, sorafenib2, TAK-6323, regorafenib4, CEP-32496, cabozantinib, and polo-like kinase inhibitors including PCM-075, volasertib, BI 2536, rigosertib (ON 01910), HMN-214, GSK461364, R03280, NMS-P937, TAK-960, cyclapolin 1, DAP-81, ZK-thiazolidinone, compound 36 (imidazopyridine derivative), LFM-A13, poloxin (thymoquinone derivative), poloxipan, purpurogallin (benzotropolone-containing compound), MLN0905, and SBE13, preferably volasertib and lapitinib.

In one embodiment, said targeted therapy compound is co-administered with a chemotherapeutic agent, and/or with a therapeutic monoclonal antibody or antigen-binding fragment thereof, and/or with a checkpoint inhibitor including CTLA-4, PD-1, and PD-L1 targeting agents, and/or with an interferon selected from Type-I IFN, Type-II IFN and Type-III IFN, and/or with a cytokine inhibitor, and/or with a small molecule drug.

In one embodiment, in said method, the level of phosphorylated TTP is reduced by administering said targeted therapy compound.

In one embodiment, said reduction is a reduction by at least 15%, preferably by at least 20%, more preferably by at least 25%.

In a further aspect, the present invention further relates to the use of phosphorylated TTP as a biomarker.

In a further aspect, the present invention further relates to the use of a targeted therapy compound selected from protein kinase inhibitors, small molecule inhibitors, and monoclonal antibody-based compounds for the manufacture of a medicament for a cancer that is characterized by an increased level of phosphorylated TTP in cancer cells compared to non-cancerous cells.

In this aspect, said targeted therapy compound, said cancer, and said increased level of phosphorylated TTP are as defined above.

BRIEF DESCRIPTION OF THE FIGURES

The present invention is now further described by reference to the following figures.

All methods mentioned in the figure descriptions below were carried out as described in detail in the examples.

1A) Characterization of the protein bands in WB with anti-TTP/ZFP36; lysates were treated with calf intestinal phosphatase (CIP) before separation on gels. Arrow indicates the phosphorylated form.

1B-1C) Determination of TTP/ZFP36 and ZFP36L1 phosphorylation patterns in MDA-MB-231 and HEK293 cells; the cells were transfected either with control, ZFP36-HA or ZFP36L1-HA vectors; lysates were treated with CIP. Western blotting was performed using anti-HA as indicated. WBs are representative blot from two experiments.

Figure 2A:
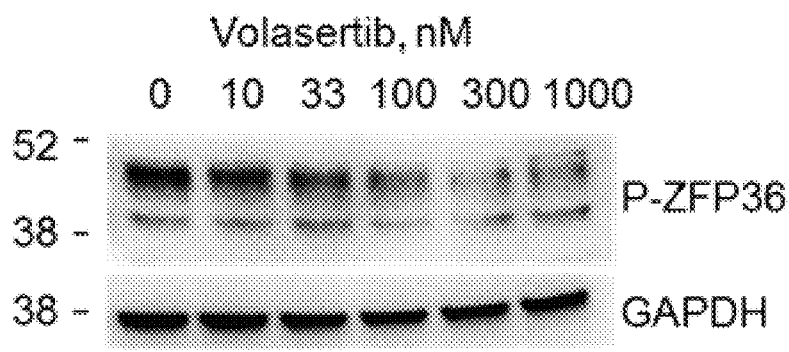
Figure 2B:
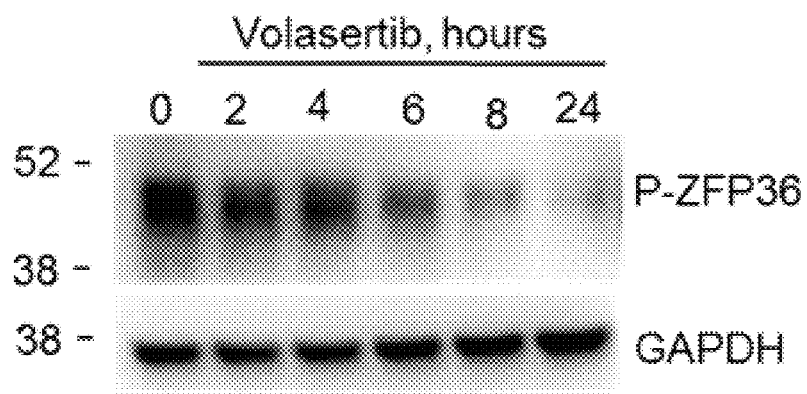
Figure 2C:
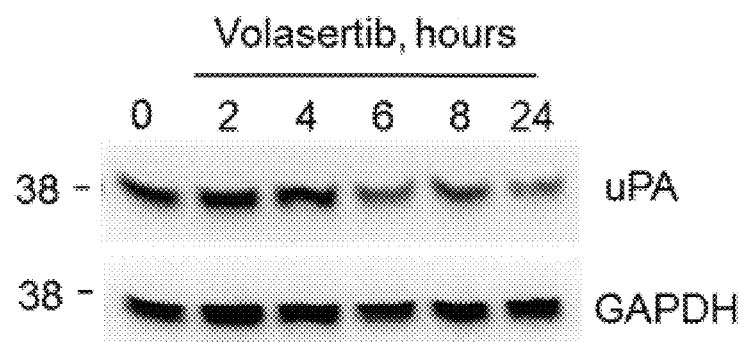

FIGS. 2A-2C show that kinase inhibition reduces phosphorylated TTP.

2A) Dose response for the PLK1 inhibitor (volasertib) effect on phosphorylated TTP level; WB shown is from one experiment of two.

2B-2C) Time course of volasertib (330 nM) action on phosphorylated TTP and its target, uPA; WBs are representative of at least two independent experiments.

Figure 3A:
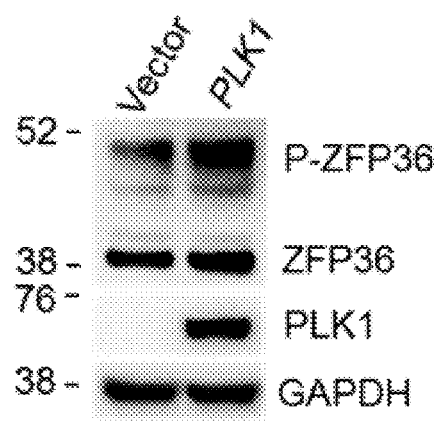
Figure 3B:
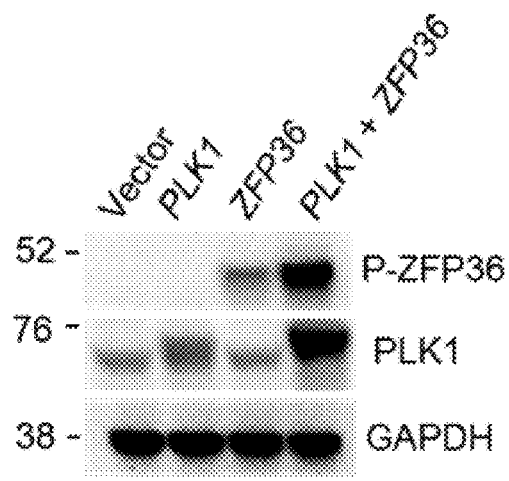
Figure 3C:
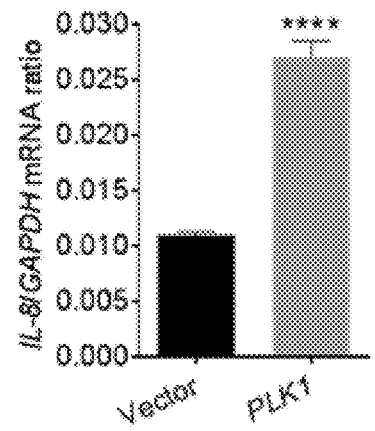

FIGS. 3A-3C show that kinase activity increases the abundance of phosphorylated ZFP36.

3A) Ectopic expression of PLK1 in MCF10A; the cells were transfected with PLK1 vector (0.5 µg/million cells) for 24 hrs. The abundance of the phosphorylated TTP/ZFP36 was evaluated by WB (one shown from two independent experiments).

3B) Co-transfection of HEK293 with PLK1 and TTP/ZFP36; the cells were co-transfected with PLK1 (0.2 µg/well) and ZFP36 (0.3 µg/million cells), then the abundance of phosphorylated ZFP36 was assessed by WB (one shown from two independent experiments).

3C) The effect of PLK1 overexpression in MCF10A cells on the endogenous IL-8 mRNA and protein expression; cells transfected with PLK1 vector (3 µg/million cells) for 24 hrs, then the IL-8 mRNA was measured using RT-QPCR. Data (Mean t SEM of replicates) from one experiment of two.

Figure 4A:
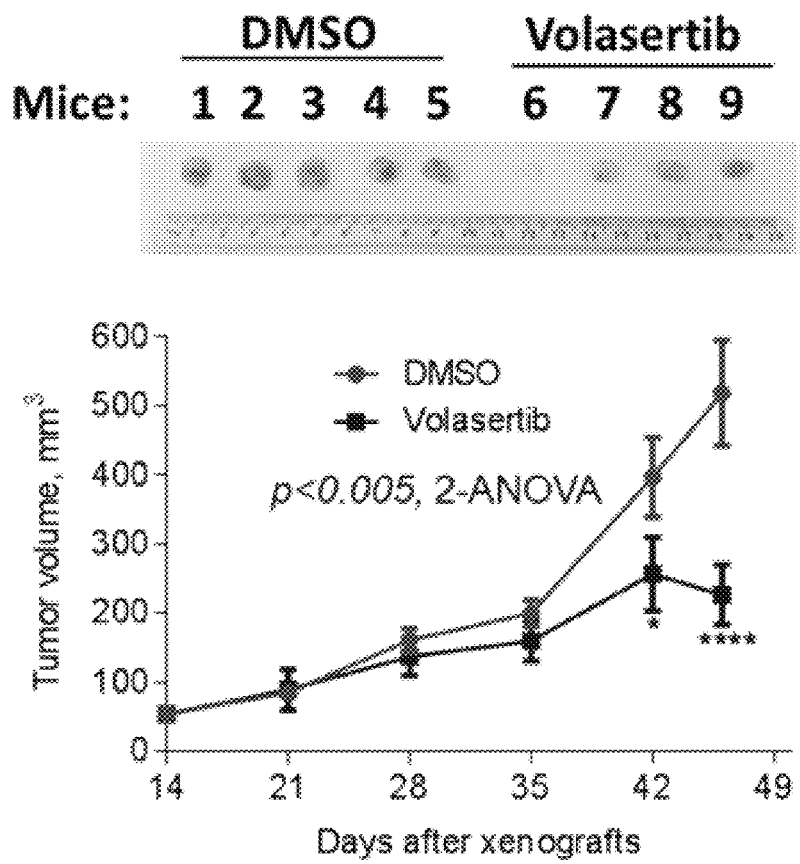
Figure 4B:
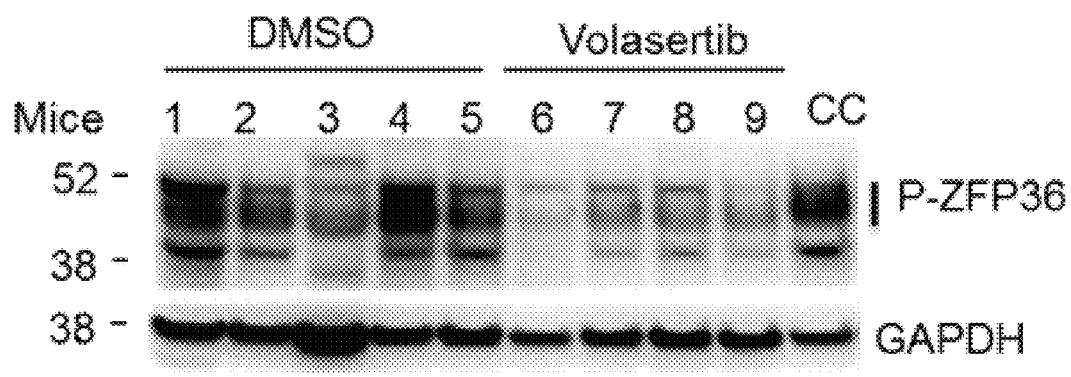

FIGS. 4A-4B show kinase inhibition in mice and reduction in TTP phosphorylation. 4A) PLK1 inhibition and tumor size in mice; MDA-MB-231 xenografts were injected into the mammary fat pad of female nude mice; when tumors become palpable, mice were treated with either volasertib (10 mg/kg) or vehicle twice weekly. The tumor size was calculated as described in Methods. Data are Mean±SEM from a nine-mouse experiment as indicated. Two-way ANOVA was performed for overall effect with Sidak's multiple comparison test (*p<0.05, ****p<0.001). 4B) The effect of volasertib on TTP/ZFP36 phosphorylation; WB of tumor tissues from each mouse as probed with anti-TTP/ZFP36 or GAPDH as the loading control.

Figure 5:
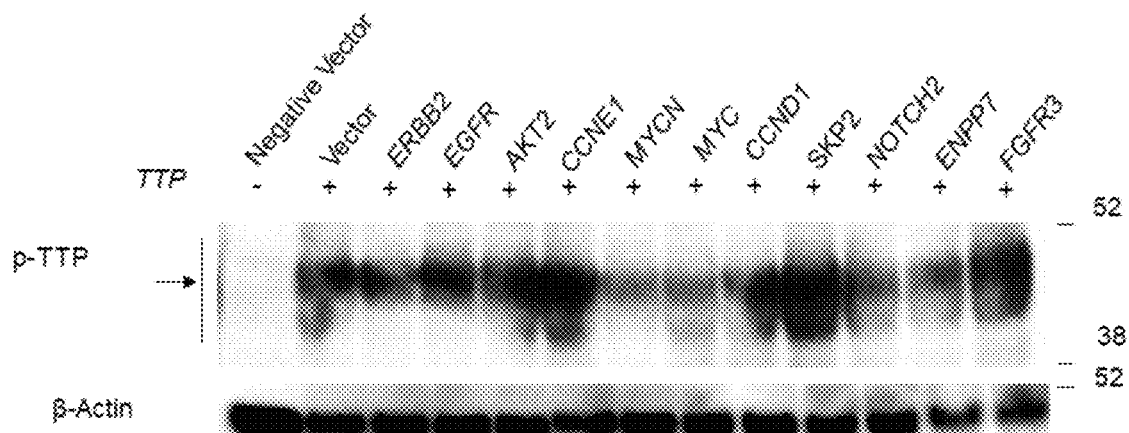

FIG. 5 shows changes in the level of phosphorylated TTP as analyzed using Western blotting. HEK293 cells were transfected with a TTP expression plasmid and with an expression plasmid encoding one of the shown cancer genes. The shown cancer genes are examples of genes known to be amplified in cancer.

Figure 6A:
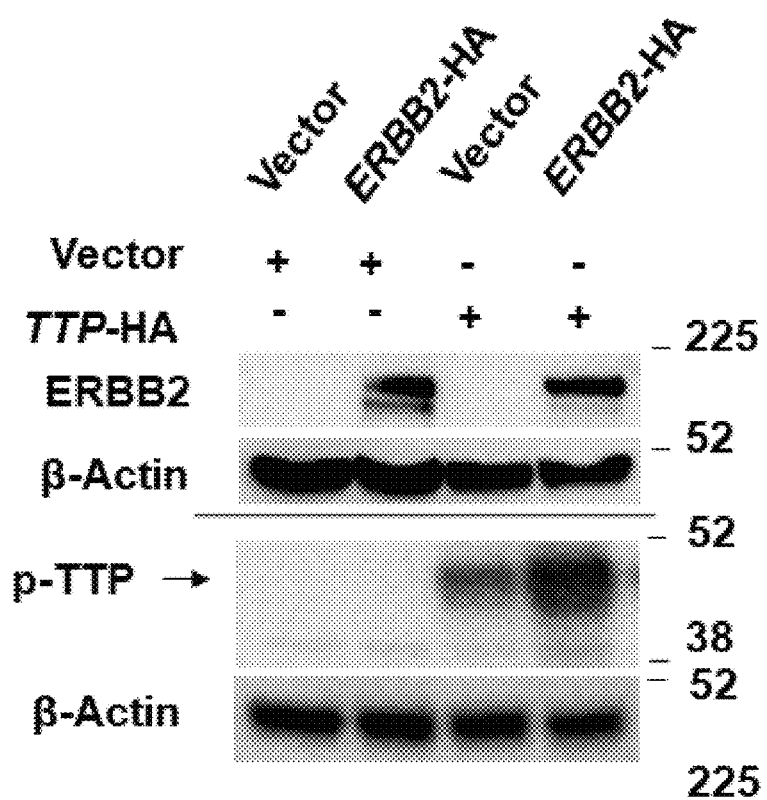
Figure 6B:
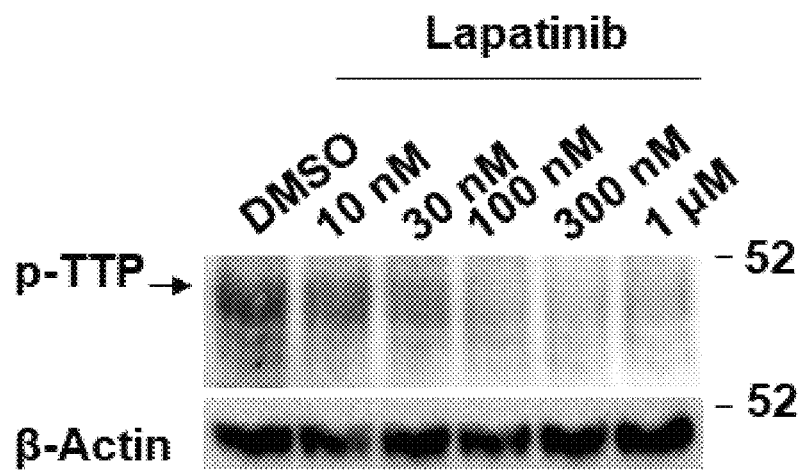
Figure 6C:
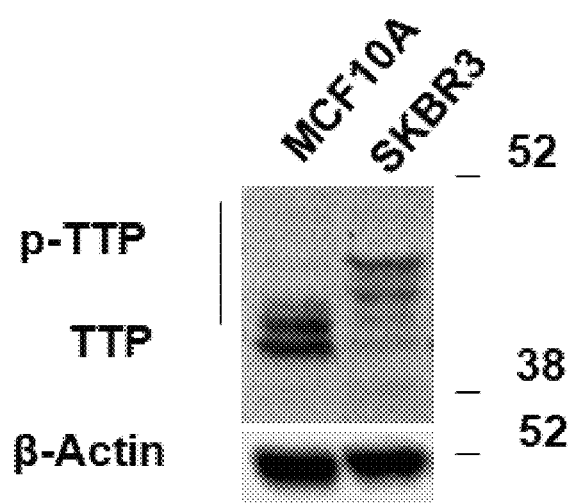

FIGS. 6A-6C shows a relation of ERBB2 and TTP phosphorylation.

6A) ERBB2 which is known to be amplified and overexpressed in Her2 (ERBB2) positive cancer is shown to increase the phosphorylated TTP in a HEK293 cell line that lacks ERBB2.

6B) The ERBB2 inhibitor, lapatinib, is shown to reduce the levels of phosphorylated TTP in the ERBB2 overexpressing breast cancer cell line SKBR3.

6C) Normal-like MCF10A breast cells have lower levels of phosphorylated TTP than SKBR3 cells having amplified (overexpressed) ERBB2.

DETAILED DESCRIPTION

The present invention relates to a novel biomarker for use in the treatment of cancer. In particular aspects, the invention relates to a targeted therapy approach and/or precision oncology tool based on the phosphorylation of the protein tristetraprolin (TTP/ZFP36) that plays a role in diseases such as cancer, chronic inflammatory conditions, and autoimmune diseases. TTP phosphorylation is herein shown to be a clinically useful biomarker for the diagnosis and prognosis of cancer. The analysis of TTP phosphorylation may be used as a cancer targeted therapy tool to select kinase inhibitors for the treatment of diseases such as cancer, particularly by monitoring whether a kinase inhibitor reduces the level of phosphorylated TTP.

Even when a drug targets a cancer subtype with a specific mutation, the therapy response varies among cancer patients, due to existence of other gene mutations and signaling aberrations. Thus, an additional "personalized" approach is needed for pinpointing a patient that will likely respond to a treatment. The present inventors herein disclose the phosphorylation of tristetraprolin (TTP/ZFP36) as a biomarker, i.e. as a diagnostic and/or therapeutic tool for drugs such as BI-3406. TTP is an RNA-binding protein that promotes the decay of the hundreds AU-rich mRNAs which are involved in cancer. In cancer, TTP activity is diminished due to phosphorylation resulting in prolongation of AU-rich mRNA half-life and subsequently overexpression of cancer proteins. TTP phosphorylation can occur due to multiple signaling pathways including both the MAPK/ERK pathway and the p38 MAPK pathway. Specifically, for example oncogenic RAS signaling can lead to TTP phosphorylation and thus increased abundance of mRNA and proteins encoded by cancer-related genes. The present inventors demonstrate that TTP phosphorylation is a highly useful tool for monitoring a drug response, such as a response towards a protein kinase inhibitor and/or RAS::SOS1 inhibitor.

The present inventors show that mice treated with an exemplary targeted therapy compound, namely a protein kinase inhibitor which is PLK1 inhibitor volasertib, reduced tumor growth. Furthermore, the present inventors demonstrate a surprising and remarkable decrease in the abundance of phosphorylated TTP/ZFP36, both in vivo and in vitro, by means of a targeted therapy compound, such as a protein kinase inhibitor. Accordingly, the present invention provides a biomarker, which is phosphorylated TTP, that can be used for analyzing whether a targeted therapy compound, such as a protein kinase inhibitor, is likely to be effective in the treatment of a disease such as cancer. Particularly, the present invention provides a biomarker which indicates, if levels of phosphorylated TTP are increased in a patient compared to a control, that a targeted therapy compound, such as a protein kinase inhibitor is likely to be effective in the treatment of said patient. Furthermore, said biomarker is a tool for selecting the targeted therapy compound from several targeted therapy compound which is likely to be most effective in a patient, namely by analyzing the response of a sample of a patient to multiple targeted therapy compound and choosing the targeted therapy compound which is most effective. Accordingly, using phosphorylated TTP as a biomarker allows for predicting and/or determining the effectiveness of a treatment.

Thus, determining the level of phosphorylated TTP in a sample of a patient, and optionally determining the response of said sample to a targeted therapy compound as determined by the level of phosphorylated TTP after treatment with the targeted therapy compound, allows for selecting the most successful targeted therapy compound for the particular patient, as well as the patient's cancer type, and is thus a useful tool for personalized medicine. In one embodiment, a targeted therapy compound is preferably a protein kinase inhibitor.

In one embodiment, TTP phosphorylation is used as a biomarker in an in vitro assay. In one embodiment, TTP phosphorylation is used as a biomarker in cancer cell lines for determining whether said cancer cell lines respond to a drug that is administered to said cell lines. In one embodiment, endogenous TTP phosphorylation is determined in KRAS-mutant cell lines. In one embodiment, the present invention relates to an antibody-based detection test for personalized medicine, in which TTP phosphorylation is analyzed prior to and after administering a drug candidate to a patient and/or to a sample of a patient.

The term "cancer", as used herein, refers to a disease characterized by dysregulated cell proliferation and/or growth. The term comprises benign and malignant cancerous diseases, such as tumors, and may refer to an invasive or non-invasive cancer. The term comprises all types of cancers, including carcinomas, sarcomas, lymphomas, germ cell tumors, and blastomas.

The term "sample", as used herein, relates to a specimen. In one embodiment, a patient sample is any of a solid sample, such as a formalin-fixed and/or paraffin-embedded tissue, a fresh tissue, a frozen tissue, and/or a patient-derived xenograft, and a liquid sample, such as a blood sample, blood total cells, circulating tumor cells, extracellular vesicles, exosomes, lymph fluid, saliva, body fluid, and/or tissue fluid.

In one embodiment, a "tumor sample" or "sample of a cancer patient", as used herein, relates to a sample of cancerous tissue of a patient, wherein said sample may derive from a solid or a non-solid cancerous tissue. The tumor sample can be in the form of dissociated cells, aspirations, tissues, tissue slices, or any other form of obtaining tumors or tumor tissues or tumor cells known to the person skilled in the art. A control sample or control value is used to estimate the relative phosphorylation levels of TTP in a diseased organ or tissue compared to a healthy organ or tissue. In one embodiment, a tumor sample comprises cancerous tissue and/or cancerous cells.

The term "cancer cell", as used herein, refers to a cell that exhibits abnormal proliferation and divides relentlessly, thereby forming a solid tumor or a non-solid tumor. In some embodiments of the present invention, cancer cell is used synonymously with "pathophysiological cell".

The term "non-cancer cell", "non-cancerous cell" or "normal cell", as used herein, refers to a cell which is not affected by aberrant expression, aberrant phosphorylation, and/or abnormal proliferation, and does not derive from cancerous tissue. In some embodiments of the present invention, the terms "normal cell" and "non-cancer cell" are used synonymously with "physiological cell".

A "control", as used herein, relates to a reference value and/or a reference sample which preferably reflect the characteristics of a healthy subject. In one embodiment, the terms "reference sample" and "control sample" are used interchangeably. A "control sample", as used herein, relates to a sample comprising normal cells, i.e. non-cancerous cells, for determining normal expression and/or phosphorylation levels in non-cancerous cells. Such a control sample may derive from the patient, wherein said control sample is taken from a healthy tissue, wherein said healthy tissue may derive from the same organ as the tumor sample of the cancerous disease, but a different site not affected by said cancerous disease, or may derive from a different organ not affected by said cancerous disease. A control sample may also relate to a sample of non-cancerous tissue of a healthy individual, or to a sample of a population of healthy individuals. In some embodiments, said control sample(s) may also relate to "control values" which reflect the normal expression and/or phosphorylation levels obtained from analysis of expression and/or phosphorylation in control samples, wherein said control samples derive from healthy tissue of the patient, or healthy tissue of a healthy individual, or healthy tissue of a population of healthy subjects.

The term "cancer-related genes" and "cancer-related proteins", as used herein, refers to genes and proteins, respectively, that are associated with cancerous diseases, and/or the development of cancerous diseases, and/or metastasis. In one embodiment, aberrant expression and aberrant phosphorylation of said cancer-related genes and cancer-related proteins, respectively, promotes formation of a cancerous disease. In one embodiment, cancer-related genes refer to proto-oncogenes.

The term "AU-rich element" or "ARE", as used herein, refers to an adenylate-uridylate-rich element in the 3' untranslated region of a mRNA. AREs are a determinant of RNA stability, and often occur in mRNAs of proto-oncogenes, nuclear transcription factors, and cytokines. TTP is an ARE-binding protein (ARE-BP) which binds to AREs and destabilizes the mRNA. The terms "increased TTP phosphorylation", "increased phosphorylation", and "increased level of phosphorylated TTP", as used herein, refer to an elevated phosphorylation level of TTP in a sample of a patient as compared to the phosphorylation level of TTP in a control, referred to as "normal phosphorylation". In some embodiments, phosphorylation is compared to normal phosphorylation in a control sample, which may derive from healthy tissue of the same individual, wherein said healthy tissue may derive from a different site of the same organ as the cancerous tissue, or from a healthy individual. In some embodiments, phosphorylation is compared to normal phosphorylation in a healthy subject population. An elevated phosphorylation level may also be referred to as "increased phosphorylation level". In one embodiment, an increased phosphorylation is an at least 5% increased phosphorylation level, preferably at least 15% increased phosphorylation level in a tumor sample compared to a control. The term "decreasing phosphorylation", as used herein, relates to decreasing elevated phosphorylation levels of TTP, to normalize said increased phosphorylation to normal phosphorylation, preferably by administering a targeted therapy compound such as a protein kinase inhibitor. In one embodiment, said decreasing phosphorylation is a decrease by at least 15%, preferably by at least 20%, more preferably by at least 25%. Methods for determining the phosphorylation level of a protein such as TTP are known to a person skilled in the art, and include western blot, ELISA, microarrays, immunohistochemistry, immunofluorescence, and mass spectrometry.

The term "normal phosphorylation" or "normal phosphorylation levels", as used herein, refers to phosphorylation levels in non-cancerous cells which are not affected by aberrant phosphorylation. In one embodiment, normal phosphorylation relates to phosphorylation levels of TTP in non-cancerous cells. In one embodiment, normal phosphorylation levels of TTP are assessed in a sample of the same subject from which the tumor sample is taken. In one embodiment, normal phosphorylation levels are assessed in a sample from a healthy subject. In one embodiment, normal phosphorylation levels are assessed in a population of healthy individuals.

The terms "normalizing" and "normalizing phosphorylation", as used herein, relate to normalizing or restoring phosphorylation levels of TTP to healthy, non-cancerous, normal phosphorylation levels, which can be achieved by administering an effective dose of a targeted therapy compound such as a protein kinase inhibitor to a patient in need thereof having abnormal phosphorylation of TTP. In one embodiment, when referring to "normalizing phosphorylation", it is meant that the level of post-transcriptional regulation of TTP phosphorylation in a cancer cell adjusts to a level of post-transcriptional regulation of TTP that is present in a non-cancerous cell, preferably by treatment with a targeted therapy compound such as a protein kinase inhibitor. In one embodiment, a "normalizing effect" refers to an effect, preferably an effect of a targeted therapy compound, which induces a normalization of abnormal TTP phosphorylation levels in cancer cells towards the TTP phosphorylation levels typically found in non-cancerous cells. In one embodiment, an "aberrant" TTP phosphorylation mean phosphorylation that deviate from "normal" phosphorylation in an individual not suffering from cancer, respectively.

The term "TTP" or "tristetraprolin", as used herein, refers to a protein which binds to AU-rich elements (AREs) in the 3'-untranslated regions of ARE-containing mRNAs, and promotes degradation of said mRNAs. TTP is also known as zinc finger protein 36 homolog (ZFP36). In one embodiment, interactions of TTP and target mRNAs are affected by the phosphorylation state of TTP. In one embodiment, phosphorylated TTP/ZFP36 is unable to promote ARE-mRNA decay, and thus the abundance of proteins involved in inflammation and cancer is increased and the half-life of these proteins is prolonged. In one embodiment, phosphorylated TTP is a biomarker for detecting whether a patient is likely to respond to a targeted therapy compound such as a protein kinase inhibitor and/or for detecting which targeted therapy compound such as a protein kinase inhibitor will have the best therapeutic effect in a patient. The term "responding to a treatment", as used herein, relates to a therapeutic effect being effectively evoked in a patient. In one embodiment, phosphorylated TTP is a biomarker to be used in personalized medicine.

The term "protein kinase", as used herein, refers to an enzyme capable of phosphorylating other proteins by transferring a phosphate group from a nucleoside triphosphate to amino acids of proteins, such as serine and threonine, and/or tyrosine. Phosphorylation of proteins may result in functional modification of said proteins by changing cellular location, activity, and/or associated with other proteins. In one embodiment, a protein kinase may relate to a serine/threonine-specific protein kinase or a tyrosine-specific protein kinase.

The term "inhibitor", as used herein, refers to an enzyme inhibitor or receptor inhibitor which is a molecule that binds to an enzyme or receptor, and decreases and/or blocks its activity, for example a protein kinase inhibitor. The term may relate to a reversible or an irreversible inhibitor. The term "small molecule inhibitor" relates to a small molecule which inhibits a signaling pathway in a patient's body, preferably a disease-related signaling pathway, more preferably a cancer-related signaling pathway. In one embodiment, a small molecule inhibitor is BI-3406.

The term "antigen-binding fragment thereof", as used herein, relates to a peptide that specifically binds to an antigen. In one embodiment, an antigen-binding fragment is based on an immunoglobulin, such as a polyclonal or monoclonal antibody, for example a substantially intact antibody, a Fab fragment, a F(ab')$_2$ fragment, a diabody, a single chain Fv fragment, a tetrabody, a triabody, a disulfide bond-stabilized Fv (dsFv), or a heavy chain VHH fragment from camels, or is based on a protein scaffold structure having antigen-binding capacity, such as an anticalin protein, an Affilin, an Affimer, an Affitin, an Alphabody, a nanobody, or a DARPin, preferably comprising antigen-binding determinants, such as a CDR, of an antibody. In one embodiment, an antibody and/or antigen-binding fragment targets phosphorylated TTP and/or TTP, i.e. specifically binds to phosphorylated TTP and/or TTP.

The term "protein kinase inhibitor", as used herein, refers to an inhibitor that blocks the action of one or more protein kinases. In one embodiment, said term relates to an inhibitor that attenuates the action of one or more protein kinases. In one embodiment, said protein kinase inhibitor is a serine/threonine protein kinase inhibitor, such as a B-Raf kinase inhibitor or a polo-like kinase inhibitor, or a tyrosine kinase inhibitor, for example a VEGFR2 inhibitor. The term "PLK-1" or "polo-like kinase 1", as used herein, refers to a specific kinase being a member of the family of polo-like kinases. A list of examples for kinase inhibitors are given in Table 2 in Example 7. In one embodiment, a protein kinase inhibitor is preferably an inhibitor of a MAP kinase, such as an inhibitor of MK2 and/or ERK, an inhibitor of AKT, and/or an inhibitor of ERBB2, such as lapitinib. In one embodiment, phosphorylated TTP is used as a biomarker for determining whether a patient, preferably a breast cancer patient, is likely to respond to a treatment with an inhibitor of ERBB2 phosphorylation, preferably lapitinib. In one embodiment, a method of determining if a patient is likely to respond to a treatment and/or a method of identifying a targeted therapy compound such as a protein kinase inhibitor for personalized medicine comprises a patient of breast cancer, preferably a HER+ breast cancer, and a targeted therapy compound being lapitinib. In one embodiment, the term "compound" and/or "targeted therapy compound" preferably relates to a protein kinase inhibitor. In one embodiment, a protein kinase inhibitor may be a small molecule and/or a monoclonal antibody-based compound.

The term "administering", as used herein, refers to applying a targeted therapy compound, such as a protein kinase inhibitor, to a target, such as a patient and/or a sample of a patient. In one embodiment, administering relates to in vitro and/or in vivo administration. In one embodiment, administering relates to intravenous, oral, nasal, mucosal, intrabronchial, intrapulmonary, intradermal, subcutaneous, intramuscular, intravascular, intrathecal, intraocular, intraarticular, intranodal, intratumoral, or intrametastatical administration of a targeted therapy compound, such as a protein kinase inhibitor to a patient in need thereof. In one embodiment, administering may also relate to in vitro administration, namely to incubating a cell and/or tissue, e.g. a sample obtained from a patient, with a targeted therapy compound such as a protein kinase inhibitor.

The term "co-administering", as used herein, refers to a combined administration of a targeted therapy compound, such as a protein kinase inhibitor with at least one other substance, such as a chemotherapeutic agent, a checkpoint inhibitor, and/or IFN, to a target such as a patient and/or sample. In one embodiment, co-administration of a targeted therapy compound, such a protein kinase inhibitor with at least one other substance allows for targeting more than one aberrant pathway.

The term "effective dose", as used herein, refers to a dose of a drug, such as a targeted therapy compound, which is in the range between the dose sufficient to evoke a therapeutic effect and the maximum tolerated dose. In one embodiment, a method of treatment of cancer according to the present invention comprises administering an effective dose of a targeted therapy compound, such as a protein kinase inhibitor to a patient in need thereof having an increased level of phosphorylated TTP compared to a control. In one embodiment, said effective dose is in a dose range established for a different method of treatment comprising administering said targeted therapy compound, such as said protein kinase inhibitor, wherein said different method of treatment is for a disease, which is not characterized by increased TTP phosphorylation levels in pathophysiological cells compared to physiological cells. In one embodiment, said protein kinase inhibitor is volasertib or lapitinib, and said effective dose is in the range of 150 mg to 300 mg once per day to once per week. In one embodiment, the terms "effective dose" and "effective amount" are used interchangeably.

The term "treating", as used herein, refers to applying a targeted therapy compound, such as a protein kinase inhibitor, to a target such as a patient and/or a sample of a patient. In one embodiment, said treating relates to in vivo treating of a patient, and/or to in vitro treating of a sample of a patient. In one embodiment, in vitro treating relates to treating a sample with a targeted therapy compound such as a protein kinase inhibitor for at least 15 min, preferably 4-8 h. In one embodiment, in vitro treating relates to treating a sample with a targeted therapy compound at a concentration of from 1 nM to 10 μM.

The term "determining a level of phosphorylated TTP", as used herein, relates assessing the level of phosphorylated TTP comprising any method capable of detecting a phosphorylation status of a protein that is known to a person skilled in the art, such as methods using reactions between an antibody (or antigen-binding fragment) and an antigen, said antigen preferably being phosphorylated TTP, for example western blotting, immunohistochemistry, immunofluorescence, mass spectrometry, flow cytometry, FACS, and ELISA. In one embodiment, said determining comprises detecting the total amount of phosphorylated TTP and/or detecting the fraction of phosphorylated TTP compared to total TTP. In one embodiment, an increased level of phosphorylated TTP relates to an increased total amount of phosphorylated TTP and/or to an increased phosphorylation degree of TTP, wherein an increased phosphorylation degree of TTP means that the ratio of phosphorylated TTP to unphosphorylated TTP is increased. In one embodiment, the level of phosphorylated TTP is determined using an antibody targeting phosphorylated TTP and/or is determined using an antibody targeting TTP. In one embodiment, if an antibody targeting TTP is used to determine the level of phosphorylated TTP, the molecular weight and/or size difference between a phosphorylated TTP and an unphosphorylated TTP is taken into account to determine the level of phosphorylated TTP, wherein phosphorylated TTP is larger than TTP, as observed, for example, with the bands obtained in western blotting. In one embodiment, phosphorylated TTP is detected by anti-phosphorylated TTP using western blotting, immunohistochemistry, immunofluorescence, or any other method capable of detecting phosphorylated TTP known to a person skilled in the art. In one embodiment, determining a level of phosphorylated TTP relates to assessing the protein level of phosphorylated TTP and/or unphosphorylated TTP. In one embodiment, phosphorylated TTP is used as a biomarker, and thus the level of phosphorylated TTP is determined in a method of determining if a patient is likely to respond to a treatment according to the present invention and/or a method of identifying a targeted therapy compound such as a protein kinase inhibitor for personalized medicine. In one embodiment, determining a level of phosphorylated TTP comprises using phosphorylated TTP as a biomarker.

The term "patient", as used herein, refers to a human or an animal having a cancer which is characterized by increased levels of phosphorylated TTP in cancer cells compared to normal cells. The terms "subject" and "individual", as used herein, are used synonymously, and relate to a human or an animal.

The term "chemotherapeutic agent", as used herein, refers to a cytotoxic agent which is of use in chemotherapy of cancer. For example, a chemotherapeutic agent may relate to an alkylating agent, such as cyclophosphamide, mechlorethamine, chlorambucil, melphalan, dacarbazine, nitrosoureas, and temozolomide, or to an anthracycline, such as daunorubicin, doxorubicin, epirubicin, idarubicin, mitoxantrone, valrubicin, or to a cytoskeletal disruptor, such as paclitaxel, docetaxel, abraxane, and taxotere, or to an epothilone, or to a histone deacetylase inhibitor, such as vorinostat and romidepsin, or to an inhibitor of topoisomerase I, such as irinotecan and topotecan, or to an inhibitor of topoisomerase II, such as etoposide, teniposide, and tafluposide, or to a kinase inhibitor, such as bortezomib, erlotinib, gefitinib, imatinib, vemurafenib, and vismodegib, or to a nucleotide analogue, such as azacitidine, azathioprine, capecitabine, cytarabine, doxifluridine, fluorouracil, gemcitabine, hydroxyurea, mercaptopurine, methotrexate, and tioguanine, or to a peptide antibiotics, such as bleomycin and actinomycin, or to a platinum-based agent, such as carboplatin, cisplatin, and oxaliplatin, or to a retinoid, such as tretinoin, alitretinoin, and bexarotene, or to a *vinca* alkaloid derivative, such as vinblastine, vincristine, vindesine, and vinorelbine. In one embodiment, in a method of treatment of cancer according to the present invention, a chemotherapeutic agent is co-administered with said targeted therapy compound such as a protein kinase inhibitor, wherein preferably, said chemotherapeutic agent is commonly used for the same type of cancer.

The term "checkpoint inhibitor", as used herein, refers to an agent used in cancer immunotherapy. A checkpoint inhibitor blocks an inhibitory immune checkpoint and thus restores immune system function, for example, an inhibitor of the immune checkpoint molecule CTLA-4, such as ipilimumab, or an inhibitor of PD-1, such as nivolumab or pembrolizumab, or an inhibitor of PD-L1, such as atezolizumab, avelumab, and durvalumab. In many of the embodiments, a checkpoint inhibitor relates to an antibody which targets a molecule involved in an immune checkpoint.

The term "interferon", or "IFN", as used herein, refers to a group of cytokines which are used for communication between cells and which trigger the immune system. Interferons comprise three classes which are Type-I interferons, Type-II interferons, and Type-III interferons. In one embodiment, said targeted therapy compound is co-administered with a Type-I, Type-II or Type-III IFN. The term "Type-I IFN", as used herein, relates to a large subgroup of interferons comprising IFN-α, IFN-β, IFN-ε, IFN-κ, IFN-τ, IFN-ζ, and IFN-ω. The term "Type-II IFN", as used herein, relates to IFN-γ. The term "Type-III IFN", as used herein, relates to IFN-λ1, 2, 3, and 4.

The terms "targeted cancer therapy" and "precision cancer therapy", as used herein, relate to the prevention or treatment of a cancer in a patient by administering an effective amount of a therapeutic agent to said patient. Preferably, prior to administering said therapeutic agent, it is tested whether the patient is likely to respond to said therapeutic agent, which is then referred to as "personalized medicine". Said cancer therapy is "targeted" (and thus "precise") since, prior to said therapy, it is determined which targeted therapy compound, for example which protein kinase inhibitor, is able to reduce increased levels of phosphorylated TTP in a cancer cell and/or tumor sample of said patient, and said normalization of TTP phosphorylation is an indicator that the cancer/cancer cells of said patient will respond to said targeted therapy compound. Accordingly, a suitable targeted therapy compound, such as a suitable protein kinase inhibitor, for treating said patient can be chosen using a method of determining if a patient is likely to respond to a treatment according to the present invention and/or a method of identifying a targeted therapy compound selected from protein kinase inhibitors, small molecule inhibitors, and monoclonal antibody-based compounds for personalized medicine according to the present invention. A method of determining if a patient is likely to respond to a treatment according to the present invention and/or a method of identifying a targeted therapy compound for personalized medicine according to the present invention are tools for precision oncology allowing for determining a suitable targeted therapy compound, such as a suitable protein kinase inhibitor, for treating a cancer patient.

The term "suitable targeted therapy compound", as used herein, relates to a targeted therapy compound being suitable for using said targeted therapy compound in a method of treatment of cancer in a patient. In one embodiment, a targeted therapy compound that is "suitable" is capable of reducing increased levels of TTP phosphorylation in a tumor sample, for example in a method of determining if a patient is likely to respond to a treatment according to the present invention and/or in a method of identifying a targeted therapy compound for personalized medicine according to the present invention. In one embodiment, a suitable targeted therapy compound is a suitable protein kinase inhibitor. In one embodiment, using phosphorylated TTP as a biomarker, for example in a method of determining if a patient is likely to respond to a treatment, allows for identifying a targeted therapy compound, e.g. a protein kinase inhibitor and/or small molecule, which is effective for treating a patient, for example by treating a patient sample with said targeted therapy compound and determining whether a therapeutic effect, e.g. a decrease in the level of phosphorylated TTP, is evoked. In one embodiment, the therapeutic effect is a decrease/reduction in the level of phosphorylated TTP.

In one embodiment, a method of determining if a patient is likely to respond to a treatment according to the present invention and/or a method of identifying a targeted therapy compound for personalized medicine according to the present invention are advantageous in that these methods are independent on the tumor type or tissue type, and in that the patient's specific cancer can be treated with one or more of the kinase inhibitor drugs identified with these methods, i.e. the suitable targeted therapy compounds can be identified prior to a treatment of a patient with a targeted therapy compound.

In one embodiment, a method of determining if a patient is likely to respond to a treatment according to the present invention and/or a method of identifying a targeted therapy compound for personalized medicine according to the present invention relate to universal single assay. The term "universal single assay", as used herein, relates to an assay which can be ubiquitously applied in the context of various cancerous diseases that involve increased levels of phosphorylated TTP. In one embodiment, a universal single assay is not only of use for a certain cancer type, but is useful for various types of cancerous diseases, and is thus a "pan-cancer" precision oncology approach.

The term "cancer-related genetic variation", as used herein, relates to a genetic variation in a DNA which is associated with a cancer, such as a mutation in an allele and/or gene, a gene amplification, a fusion of genes, a deletion of an allele and/or gene. In one embodiment, a cancer-related genetic variation is any of a mutation in KRAS, an amplification of EGFR, an EGFR exon 19 deletion, an EGFR exon 21 L858R alteration, an ALK fusion gene, a BRAF V600E and V600K alteration, an ERBB2 copy number alteration, a HER2 gene amplification, a KRAS/NRAS wild-type, and a NTRK1/2/3 fusion gene. In one embodiment, if a patient sample has a KRAS mutation in the DNA, and there is an increased level of phosphorylated TTP in the sample, then the patient is likely to benefit from a KRAS inhibitor. In one embodiment, if a patient sample has an EGFR amplification in the DNA, and there is an increased level of phosphorylated TTP in the sample, the patient is likely to benefit from an EGFR kinase inhibitor. In one embodiment, a method of the present invention comprises determining the level of phosphorylated TTP in a patient and/or a patient's tumor sample, and determining whether said patient has a genetic variation. In one embodiment, if a patient and/or a patient's tumor sample has/have an increased level of phosphorylated TTP, and said patient has a genetic variation, such as a KRAS mutation and/or an EGFR amplification, said patient is likely to respond to a treatment with a targeted therapy compound, preferably a protein kinase inhibitor. In one embodiment, if a method of determining if a patient is likely to respond to a treatment is carried out without treating a tumor sample with one or more targeted therapy compound(s), said method preferably further comprises determining a cancer-related genetic variation. In one embodiment, the presence of a genetic variation, e.g. mutation, in a patient and/or a patient's sample, in addition to an increased level of phosphorylated TTP, is a strong indicator that a targeted therapy compound, preferably a protein kinase inhibitor, will be effective in treating said patient. In one embodiment, a genetic variation is a variation and/or mutation in any of the targets as specified in Table 1 in Example 6 and/or any of the targets as specified in Table 2 in Example 7. In one embodiment, the presence of a genetic variation, e.g. mutation, in a target as specified in Table 1 and/or Table 2 in a patient and/or a patient's sample, in addition to an increased level of phosphorylated TTP, indicates that a targeted therapy compound, such as the targeted therapy compound listed in Table 1 and/or Table 2 for the respective target, will be effective in treating said patient.

The term "method of determining if a patient is likely to respond to a treatment", as used herein, relates to a method in which it is determined whether a patient will respond to a treatment with a targeted therapy compound, such as a protein kinase inhibitor. In one embodiment, the method of determining further comprises taking into account whether the patient's DNA has cancer-related genetic variations, such as mutations.

The term "determining a cancer-related genetic variation", as used herein, relates to assessing whether a patient has a genetic variation that is typically associated with a risk of obtaining a cancer. In one embodiment, determining a cancer-related genetic variation relates to determining a cancer biomarker in a tumor sample of a patient other than the biomarker being phosphorylated TTP. In one embodiment, such a genetic variation determined is a KRAS mutation and/or an EGFR amplification. In one embodiment, the methods of the present invention comprise determining at least two biomarkers in a tumor sample of a patient, said two biomarkers being, firstly, phosphorylated TTP, and, secondly, a biomarker other than phosphorylated TIP, e.g. a genetic variation. In one embodiment, said cancer-related genetic variation is determined using the sample in which the level of phosphorylated TTP is determined, or using a sample different from the sample in which the level of phosphorylated TTP is determined, but a sample obtained from the same patient. In one embodiment, a cancer-related genetic variation and the level of phosphorylated TTP are determined simultaneously, optionally in the same step, or subsequently. In one embodiment, a cancer-related genetic variation is determined using genotyping and/or DNA sequencing. In one embodiment, a genetic variation is a genetic variation in any of the targets listed in Table 1 and/or Table 2.

The term "monitoring a treatment response", as used herein, relates to evaluating the therapeutic success of a treatment. The monitoring of the treatment response comprises obtaining samples from a first time point and a second time point, wherein the second time point is later in the period of treatment than the first time point, and comparing the levels of phosphorylated TTP determined for the first time point and the second time point. If the level of phosphorylated TTP decreases during the treatment period, i.e. from a first time point to a second time point, the treatment, i.e. the protein kinase inhibitor administered to a patient, is successful in treating said patient.

The term "targeted therapy compound", as used herein, relates to a drug selected from protein kinase inhibitors, small molecule inhibitors, and monoclonal antibody-based compounds, preferably a drug which is used for targeted therapy, i.e. personalized medicine. In one embodiment, a targeted therapy compound is a protein kinase inhibitor, a small molecule inhibitor, and/or a monoclonal antibody-based compound. The term "monoclonal antibody-based compound", as used herein, relates to monoclonal antibodies as well as antigen-binding fragments thereof, such as Fab fragments, $F(ab)_2$ fragments, scFV fragments, diabodies, triabodies, scFv-Fc fragments, monobodies, and VhH fragments. In one embodiment, a targeted therapy compound is preferably a protein kinase inhibitor.

In the following, reference is made to the examples, which are given to illustrate, not to limit the present invention.

EXAMPLES

Example 1: Materials and Methods

Cell Lines

Breast cancer cell lines MDA-MB-231, the normal-like breast cell line MCF10A, and the HEK293 kidney cell line were obtained from American Type Culture Collection (ATCC, Rockville, Md., USA). MDA-MB-231 and HEK293 cells were cultured in Dulbecco's modified Eagle's medium (DMEM; Invitrogen, Carlsbad, Calif., USA) at 37° C. supplemented with 2 mM glutamine and 10% fetal bovine serum (FBS). MCF10A cells were maintained in Ham's F12-DMEM mixture (Thermo Fisher Scientific, Waltham, Mass., USA) and supplemented with 20 ng/ml epidermal growth factor (EGF), 0.01 mg/ml bovine insulin and 500 ng/ml hydrocortisone (Sigma, St. Louis, Mo., USA). All culture media were supplemented with 1% penicillin-streptomycin antibiotics (Sigma-Aldrich).

Plasmids and Transfections

PLK1 expression vector was obtained from Genecopoeia (Rockville, Md., US); vector expressing human hemagglutinin (HA)-tagged ZFP36 (TTP) was described previously, and HA-tagged ZFPL36L1 (BRF1) was cloned by PCR from cDNA in a CMV-driven expression vector.

Quantitative Reverse Transcription-Polymerase Chain Reaction and mRNA Half-Life

Total RNA was extracted using Trizol reagent (TRI Reagent, Sigma-Aldrich). The cells were lysed directly on the culture dish by adding 1 ml of the TRI Reagent per 10 $cm^2$ surface area. Reverse transcription for preparation of cDNA was performed using 3 µg of total RNA, 150 ng random primers, 0.1 M dithiothreitol (DTT), 10 mM deoxynucleotide triphosphate (dNTP) and 200 U of SuperScript II (Invitrogen, Foster City, Calif.). The quantitative RT-QPCR was performed in multiplex in the Chroma 4 DNA Engine cycler (BioRad, Hercules, Calif., USA) using FAM-labelled TaqMan probes (Applied Biosystems, Foster City, Calif., USA) for IL-8 while a VIC-labelled glyceraldehyde-3-phosphate dehydrogenase (GAPDH) probe was used as the endogenous control. Samples were amplified in triplicate, and quantification of relative expression was performed using the estimation of quantitation cycle (Cq) method.

Western Blotting and TTP Phosphorylation

The cells were lysed in a mixture of 0.5% NP40 buffer, protease inhibitor and phosphatase inhibitor. The calf intestinal alkaline phosphatase (CIP, Promega, Madison, Wis., USA) was used to verify the phosphorylation status of TTP/ZFP36, 20 units were added to the cell lysate (per 250 ul). The cell lysates were loaded and subjected to electrophoresis on 4-12% NuPAGE Bis-Tris gel (Invitrogen, Foster City, Calif., USA). Then, the proteins were transferred from the gel to nitrocellulose membranes (Hybond ECL; Amersham Biosciences, Piscataway, N.J.) in the presence of NuGAGE 20× transfer buffer (Invitrogen, Foster City, Calif., USA). After blocking, membranes were incubated with primary antibodies diluted in 5% bovine serum albumin (BSA) (Sigma-Aldrich, St Louis, Mo.) at 4° C. overnight. For TTP/ZFP36, a custom-made affinity purified TTP polyclonal antibody and against C-terminal end of TTP and was used previously [5]. This antibody is specific to TTP/ZFP36, but not the ortholog ZFP36L1 when using 0.5% NP40 buffer instead of Laemmli buffer. Other antibodies are: anti-PLK1 (dilution 1:1000, Cell signaling, Massachusetts, USA), anti-GAPDH (dilution 1:500, Abcam, MA, USA), anti-HA, dilution 1:5000, Roche, Upper Bavaria, Germany). Thereafter, the membranes were incubated with corresponding secondary antibodies (diluted in 5% BSA, 1:2000 dilution) (Santa Cruz Biotech, Santa Cruz, Calif.) for 1-3 hrs. Protein bands were detected using ECL Western blotting detection reagents (Amersham Biosciences, Amersham, UK) in Molecular Imager ChemiDoc machine (BioRad, Hercules, Calif., USA).

Animal Studies

Nude mice were purchased from Jackson Laboratories (Bar Harbor, Me., USA). The mice were housed at the animal facility at King Faisal Specialist Hospital and Research Center (KFSHRC) and maintained in accordance with protocols approved by the institution Animal Care and Use Committee. One million MDA-MB-231 cells were suspended in 100 µl of PBS:Matrigel (1:1 ratio), then injected into the 4th mammary fat pad of female mice (8 weeks old) after they were anesthetized with Isoflurane. Tumors were allowed to grow for 1 week before treatment with volasertib (10 mg/kg) or DMSO alone (n=5 mice per group). Treatment was administered via intraperitoneal route twice a week for four weeks after which mice were sacrificed and tumors collected for RNA and protein analyses. Tumor growth was measured by caliper, and the volume was calculated by the formula ($\pi/6 \times L \times M2$), where L and M refer to the large and small diameters of each tumor, respectively. Mice weight and tumor size were recorded weekly.

Statistical Analysis

Data are presented as Means±standard error of the mean (SEM). Two-tailed student's t-test was used when comparing two columns of data. Two-way analysis of variance was used to analyze two groups of data, each having two data columns. The analyses were performed using GraphPad Prism.

Example 2: ZFP36 Phosphorylation in Cancer Cells

Figure 1A:
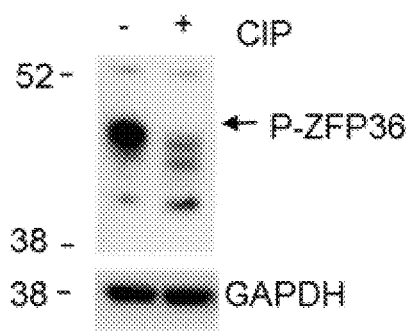
FIGS. 1A-1C show phosphorylated TTP status in cancer cells.
Figure 1B:
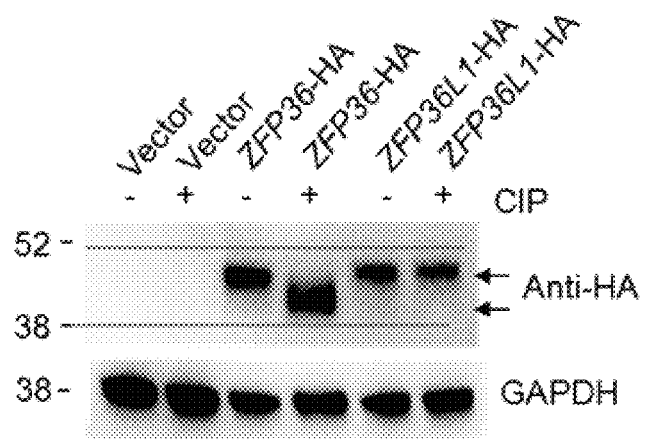
Figure 1C:
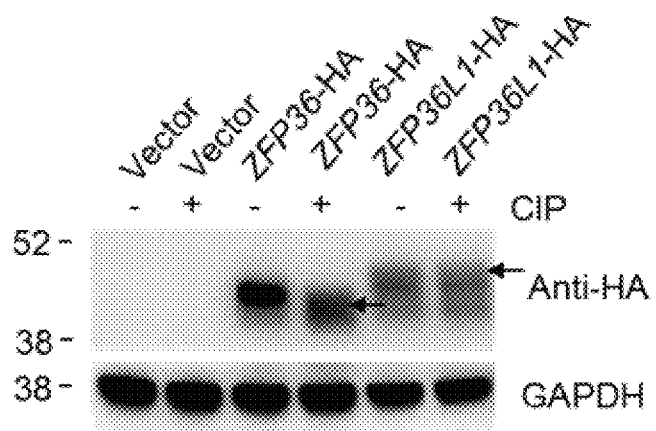

TTP is an ARE-binding and mRNA decay-promoting protein that is inhibited by phosphorylation. The present inventors analysed the effect of PLK1 pharmacological targeting on TTP phosphorylation. First, by using sensitive and specific Western blotting for both unphosphorylated and phosphorylated TTP, the present inventors observed that in the triple-negative MDA-MB-231 cell line, TTP largely existed as a high molecular weight species. Treatment with CIP reduced its size, indicating the phosphorylation status (FIG. 1A). Ectopically over-expressed TTP became phosphorylated in MDA-MB-231 and HEK293 cells, since treatment with CIP reduces its size (FIG. 1B). While the CIP treatment of cells transfected with ZFP36L1 (BRF1), ZFP36L1 being a protein different from ZFP36 but belonging to the same family as ZFP36, did not lead to a similar effect (FIGS. 1B and C). Both proteins are tagged with HA, allowing probing of both with antibody to HA.

When detecting by Western blotting, sizes of larger than the expected size (~40 kDa) indicate phosphorylated forms. Alternatively, Western blotting can be performed in two steps, immunoprecipitation by anti-TTP, followed by immunoblot with anti-phosphoserine. Any phosphorylated site antibody can be used since TTP has numerous potential phosphorylated sites. There are many serine and threonine conserved sites (estimated more than 30) in TTP protein that be potentially phosphorylated. Currently, there are no commercially available anti-phosphorylated TTP, but, can be developed to any phosphorylatable sites in TTP protein. This would facilitate immunohistochemistry or immunofluorescence particularly on patient's issues. Examples of amino acids that are predicted to be phosphorylated in the sequence of TTP (SEQ ID NO. 1) include but are not limited to serine residues numbers 9, 12, 14, 21, 28, 29, 34, 35, 39, 41, 43, 45, 46, 48, 42, 52, 58, 60, 66, 88, 90, 93, 98, 99, 102, 113, 115, 160, 169, 184, 186, 188, 192, 197, 207, 209, 113, 210, 211, 212, 216, 214, 217, 218, 228, 230, 233, 252, 260, 273, 276, 279, 286, 287, 289, 290, 294, 296, 323, and 325, threonine residues numbers 4, 26, 59, 92, 95, 97, 99, 100, 106, 111, 196, 238, 246, 257, and 271, and tyrosine residues numbers 120, 151, 158, and 284.

Example 3: Kinase Inhibitor Reducing the Phosphorylation of TTP

An exemplary kinase inhibitor, namely volasertib, was tested for the effects on the level of phosphorylation of TTP. Volasertib reduced in a dose-dependent manner the abundance of total TTP and phosphorylated TTP. The maximum dosage tested was 300 nM, and the lowest tested dose was 10 nM and was still effective (FIG. 2A). The time course showed that the effect was observed as early as 2 hrs after treatment and maximal at 8 hrs after treatment (FIG. 2B). There was no change in the mobility of ZFP36 as observed with CIP treatment, indicating a partial, rather than complete de-phosphorylation event (as with CIP). The abundance of the uPA protein was also reduced by volasertib (FIG. 2C).

Table 2 shows a list of other kinase inhibitors useful in reducing the level of phosphorylated TTP.

Example 4: Kinase Activity Increases the Abundance of Phosphorylated ZFP36

The effects of kinase activity on TTP phosphorylation in cancer were further analyzed with regard to polo like kinase 1 (PLK1). PLK1 was over-expressed in MCF10A normal-like cells, which express low PLK1 levels compared to tumor cells. PLK1 caused an increased abundance of the phosphorylated TTP/ZFP36 (FIG. 3A). Moreover, using HEK293 cell line, which has non-detectable amounts of PLK1 and TTP/ZFP36 proteins, the present inventors showed that co-expression of PLK1 and TTP/ZFP36 led to increased abundance of the phosphorylated ZFP36 protein (FIG. 3B). It was observed that PLK1 also increased in the presence of the phosphorylated TTP/ZFP36. Co-transfection with SGFP did not affect the fluorescence levels due to PLK1 indicating the increase in the ZFP36 phosphorylation is not due to changes in transfection efficiency (data not shown). PLK1 expression in MCF10A caused an increase in the abundance of IL-8 mRNA, which is TTP target (FIG. 3C) and also in secreted levels as measured by ELISA (FIG. 3D).

Example 5: The Effect of Kinase Inhibition on TTP/ZFP36 Phosphorylation in the Tumor Xenografts in Nude Mice To study the effect of kinase inhibition on TTP phosphorylation in vivo and the subsequent effect on tumor growth, MDA-MB-231 xenografts were injected into the mammary fat pad of female nude mice. The kinase inhibitor volasertib (10 mg/kg) or vehicle was administered bi-weekly upon the formation of palpable tumors. While the tumors in the control group continued to grow, those in the treatment group demonstrated a slower growth rate and began to regress by the end of the experiment (FIG. 4A, upper panel). A statistically significant difference in tumor volume could be seen after 4 weeks of treatment (FIG. 4A, lower panel). These results clearly demonstrate the role of PLK1 inhibition on tumor progression of MDA-MB-231 breast cancer cells. Next, the present inventors examined the in vivo effect of volasertib on phosphorylated TTP protein abundance in the excised tumor tissues. The amounts of the phosphorylated TTP/ZFP36 levels in the mice tissues were markedly reduced due to the in vivo volasertib treatment (FIG. 4B, lanes 6-9) compared with the control (lanes, 1-5), which clearly substantiates the in vitro data.

Example 6: Exemplary Targeted Therapy Compounds and Corresponding Targets/Indications The list in Table 1 below shows examples of targeted therapy compounds which can be tested in a method of determining if a patient is likely to respond to a treatment according to the present invention, and/or in a method of identifying a targeted therapy compound for personalized medicine according to the present invention. Furthermore, the examples of targeted therapy compounds in Table 1 are exemplary targeted therapy compounds that can be used in a method of treatment of cancer in a patient.

TABLE 1

Examples of targeted therapy compounds, their targets, and FDA-approved indications.

| Agent | Target(s) | FDA-approved indication(s) |
|---|---|---|
| Monoclonal antibodies | | |
| bevacizumab | humanized monoclonal antibody with a circulatory system target (VEGF-A) | |
| cetuximab | chimeric monoclonal antibody with a tumor target (EGFR) | |
| ipilimumab | fully human antibody with an immune system target (CTLA-4) | |
| Small molecules | | |
| bortezomib | small molecule proteasome inhibitor | |
| imatinib | small molecule tyrosine kinase inhibitor | |
| seliciclib | small molecule cyclin-dependent kinase inhibitor | |
| Ado-trastuzumab emtansine (Kadcyla) | HER2 (ERBB2/neu) | Breast cancer (HER2+) |
| Afatinib (Gilotrif) | EGFR (HER1/ERBB1), HER2 (ERBB2/neu) | Non-small cell lung cancer (with EGFR exon 19 deletions or exon 21 substitution (L858R) mutations) |
| Aldesleukin (Proleukin) | | Renal cell carcinoma Melanoma |

TABLE 1-continued

Examples of targeted therapy compounds, their targets, and FDA-approved indications.

| Agent | Target(s) | FDA-approved indication(s) |
|---|---|---|
| Alectinib (Alecensa) | ALK | Non-small cell lung cancer (with ALK fusion) |
| Alemtuzumab (Campath) | CD52 | B-cell chronic lymphocytic leukemia |
| Atezolizumab (Tecentriq) | PD-L1 | Urothelial carcinoma |
| Aveluniab (Bavencio) | PD-L1 | Non-small cell lung cancer<br>Merkel cell carcinoma<br>Urothelial cancer |
| Axitinib (Inlyta) | KIT, PDGFRβ, VEGFR1/2/3 | Renal cell carcinoma |
| Belimumab (Benlysta) | BAFF | Lupus erythematosus |
| Belinostat (Beleodaq) | HDAC | Peripheral T-cell lymphoma |
| Bevacizumab (Avastin) | VEGF ligand | Cervical cancer<br>Colorectal cancer<br>Fallopian tube cancer<br>Glioblastoma<br>Non-small cell lung cancer<br>Ovarian cancer<br>Peritoneal cancer<br>Renal cell carcinoma |
| Blinatumomab (Blincyto) | CD19/CD3 | Acute lymphoblastic leukemia (precursor B-cell) |
| Bortezomib (Velcade) | Proteasome | Multiple myeloma<br>Mantle cell lymphoma |
| Bosutinib (Bosulif) | ABL | Chronic myelogenous leukemia (Philadelphia chromosome positive) |
| Brentuximab vedotin (Adcetris) | CD30 | Hodgkin lymphoma<br>Anaplastic large cell lymphoma |
| Brigatinib (Alunbrig) | ALK | Non-small cell lung cancer (ALK+) |
| Cabozantinib (Cabometyx [tablet], Cometriq [capsule]) | FLT3, KIT, MET, RET, VEGFR2 | Medullary thyroid cancer<br>Renal cell carcinoma |
| Canakinumab (Ilaris) | IL-1β | Juvenile idiopathic arthritis<br>Cryopyrin-associated periodic syndromes |
| Carfilzomib (Kyprolis) | Proteasome | Multiple myeloma |
| Ceritinib (Zykadia) | ALK | Non-small cell lung cancer (with ALK fusion) |
| Cetuximab (Erbitux) | EGFR (HER1/ERBB1) | Colorectal cancer (KRAS wild type)<br>Squamous cell cancer of the head and neck |
| Cobimetinib (Cotellic) | MEK | Melanoma (with BRAF V600E or V600K mutation) |
| Crizotinib (Xalkori) | ALK, MET, ROS1 | Non-small cell lung cancer (with ALK fusion or ROS1 gene alteration) |
| Dabrafenib (Tafinlar) | BRAF | Melanoma (with BRAF V600 mutation)<br>Non-small cell lung cancer (with BRAF V600E mutation) |
| Daratumumab (Darzalex) | CD38 | Multiple myeloma |
| Dasatinib (Sprycel) | ABL | Chronic myelogenous leukemia (Philadelphia chromosome positive)<br>Acute lymphoblastic leukemia (Philadelphia chromosome positive) |
| Denosumab (Xgeva) | RANKL | Giant cell tumor of the bone |
| Dinutuximab (Unituxin) | B4GALNT1 (GD2) | Pediatric neuroblastoma |
| Durvalumab (Imfinzi) | PD-L1 | Urothelial carcinoma<br>Non-small cell lung cancer |
| Elotuzumab (Empliciti) | SLAMF7 (CS1/CD319/CRACC) | Multiple myeloma |
| Enasidenib (Idhifa) | IDH2 | Acute myeloid leukemia (with IDH2 mutation) |
| Erlotinib (Tarceva) | EGFR (HER1/ERBB1) | Non-small cell lung cancer (with EGFR exon 19 deletions or exon 21 substitution (L858R) mutations)<br>Pancreatic cancer |
| Everolimus (Afinitor) | mTOR | Pancreatic, gastrointestinal, or lung origin neuroendocrine tumor<br>Renal cell carcinoma<br>Nonresectable subependymal giant cell astrocytoma associated with |

TABLE 1-continued

Examples of targeted therapy compounds, their targets, and FDA-approved indications.

| Agent | Target(s) | FDA-approved indication(s) |
|---|---|---|
| | | tuberous sclerosis<br>Breast cancer (HR+, HER2−) |
| Gefitinib (Iressa) | EGFR (HER1/ERBB1) | Non-small cell lung cancer (with EGFR exon 19 deletions or exon 21 substitution (L858R) mutations) |
| Ibritumomab tiuxetan (Zevalin) | CD20 | Non-Hodgkin's lymphoma |
| Ibrutinib (Imbruvica) | BTK | Mantle cell lymphoma<br>Chronic lymphocytic leukemia<br>Waldenstrom's macroglobulinemia |
| Idelalisib (Zydelig) | PI3Kδ | Chronic lymphocytic leukemia<br>Follicular B-cell non-Hodgkin lymphoma<br>Small lymphocytic lymphoma |
| Imatinib (Gleevec) | KIT, PDGFR, ABL | GI stromal tumor (KIT+)<br>Dermatofibrosarcoma protuberans<br>Multiple hematologic malignancies including Philadelphia chromosome-positive ALL and CML |
| Ipilimumab (Yervoy) | CTLA-4 | Melanoma<br>Renal cell carcinoma |
| Ixazomib (Ninlaro) | Proteasome | Multiple Myeloma |
| Lapatinib (Tykerb) | HER2 (ERBB2/neu), EGFR (HER1/ERBB1) | Breast cancer (HER2+) |
| Lenvatinib (Lenvima) | VEGFR2 | Renal cell carcinoma<br>Thyroid cancer |
| Midostaurin (Rydapt) | FLT3 | acute myeloid leukemia (FLT3+) |
| Necitumumab (Portrazza) | EGFR (HER1/ERBB1) | Squamous non-small cell lung cancer |
| Neratinib (Nerlynx) | HER2 (ERBB2/neu) | Breast cancer (HER2 overexpressed/amplified) |
| Nilotinib (Tasigna) | ABL | Chronic myelogenous leukemia (Philadelphia chromosome positive) |
| Niraparib (Zejula) | PARP | Ovarian cancer<br>Fallopian tube cancer<br>Peritoneal cancer |
| Nivolumab (Opdivo) | PD-1 | Colorectal cancer (dMMR and MSI-H)<br>Head and neck squamous cell carcinoma<br>Hepatocellular carcinoma<br>Hodgkin lymphoma<br>Melanoma<br>Non-small cell lung cancer<br>Renal cell carcinoma<br>Urothelial carcinoma |
| Obinutuzumab (Gazyva) | CD20 | Chronic lymphocytic leukemia<br>Follicular lymphoma |
| Ofatumumab (Arzerra, HuMax-CD20) | CD20 | Chronic lymphocytic leukemia |
| Olaparib (Lynparza) | PARP | Ovarian cancer (with BRCA mutation) |
| Olaratumab (Lartruvo) | PDGFRα | Soft tissue sarcoma |
| Osimertinib (Tagrisso) | EGFR | Non-small cell lung cancer (with EGFR T790M mutation) |
| Palbociclib (Ibrance) | CDK4, CDK6 | Breast cancer (HR+, HER2−) |
| Panitumumab (Vectibix) | EGFR (HER1/ERBB1) | Colorectal cancer (KRAS wild type) |
| Panobinostat (Farydak) | HDAC | Multiple myeloma |
| Pazopanib (Votrient) | VEGFR, PDGFR, KIT | Renal cell carcinoma |
| Pembrolizumab (Keytruda) | PD-1 | Classical Hodgkin lymphoma<br>Colorectal cancer (MSI-H/dMMR)<br>Gastric cancer<br>Melanoma<br>Non-small cell lung cancer (PD-L1+)<br>Head and neck squamous cell carcinoma<br>Urothelial cancer<br>Solid tumors (MSI-H/dMMR) |
| Pertuzumab (Perjeta) | HER2 (ERBB2/neu) | Breast cancer (HER2+) |
| Ponatinib (Iclusig) | ABL, FGFR1-3, FLT3, VEGFR2 | Chronic myelogenous leukemia<br>Acute lymphoblastic leukemia (Philadelphia chromosome positive) |

TABLE 1-continued

Examples of targeted therapy compounds, their targets, and FDA-approved indications.

| Agent | Target(s) | FDA-approved indication(s) |
|---|---|---|
| Ramucirumab (Cyramza) | VEGFR2 | Colorectal cancer |
|  |  | Gastric cancer or Gastroesophageal junction (GEJ) adenocarcinoma |
|  |  | Non-small cell lung cancer |
| Regorafenib (Stivarga) | KIT, PDGFRβ, RAF, RET, VEGFR1/2/3 | Colorectal cancer |
|  |  | Gastrointestinal stromal tumors |
|  |  | Hepatocellular carcinoma |
| Ribociclib (Kisqali) | CDK4, CDK6 | Breast cancer (HR+, HER2−) |
| Rituximab (Rituxan, Mabthera) | CD20 | Non-Hodgkin's lymphoma |
|  |  | Chronic lymphocytic leukemia |
|  |  | Rheumatoid arthritis |
|  |  | Granulomatosis with polyangiitis |
| Rituximab/hyaluronidase human (Rituxan Hycela) | CD20 | Chronic lymphocytic leukemia |
|  |  | Diffuse large B-cell lymphoma |
|  |  | Follicular lymphoma |
| Romidepsin (Istodax) | HDAC | Cutaneous T-cell lymphoma |
|  |  | Peripheral T-cell lymphoma |
| Rucaparib (Rubraca) | PARP | Ovarian cancer (with BRCA mutation) |
| Ruxolitinib (Jakafi) | JAK1/2 | Myelofibrosis |
| Siltuximab (Sylvant) | IL-6 | Multicentric Castleman's disease |
| Sipuleucel-T (Provenge) |  | Prostate cancer |
| Sonidegib (Odomzo) | Smoothened | Basal cell carcinoma |
| Sorafenib (Nexavar) | VEGFR, PDGFR, KIT, RAF | Hepatocellular carcinoma |
|  |  | Renal cell carcinoma |
|  |  | Thyroid carcinoma |
| Temsirolimus (Torisel) | mTOR | Renal cell carcinoma |
| Tocilizumab (Actemra) | IL-6R | Rheumatoid arthritis |
|  |  | Juvenile idiopathic arthritis |
| Tofacitinib (Xeljanz) | JAK3 | Rheumatoid arthritis |
| Tositumomab (Bexxar) | CD20 | Non-Hodgkin's lymphoma |
| Trametinib (Mekinist) | MEK | Melanoma (with BRAF V600 mutation) |
|  |  | Non-small cell lung cancer (with BRAF V600E mutation) |
| Trastuzumab (Herceptin) | HER2 (ERBB2/neu) | Breast cancer (HER2+) |
|  |  | Gastric cancer (HER2+) |
| Vandetanib (Caprelsa) | EGFR (HER1/ERBB1), RET, VEGFR2 | Medullary thyroid cancer |
| Vemurafenib (Zelboraf) | BRAF | Melanoma (with BRAF V600 mutation) |
| Venetoclax (Venclexta) | BCL2 | Chronic lymphocytic leukemia (with 17p deletion) |
| Vismodegib (Erivedge) | PTCH, Smoothened | Basal cell carcinoma |
| Vorinostat (Zolinza) | HDAC | Cutaneous T-cell lymphoma |
| Ziv-aflibercept (Zaltrap) | PlGF, VEGFA/B | Colorectal cancer |

Example 7: Exemplary Protein Kinase Inhibitors

The list in Table 2 below shows examples of protein kinase inhibitors which can be tested in a method of determining if a patient is likely to respond to a treatment according to the present invention and/or a method of identifying a targeted therapy compound for personalized medicine according to the present invention. Furthermore, the examples of protein kinase inhibitors in Table 2 are exemplary inhibitors that can be used in a method of treatment of cancer in a patient.

TABLE 2

Examples of kinase inhibitors and their targets.

| Kinase inhibitor | Target |
|---|---|
| (−)-BAY-1251152 | CDK |
| (−)-Indolactam V | PKC |
| (+)-BAY-1251152 | CDK |
| (±)-Zanubrutinib | Btk |
| (1S,3R,5R)-PIM447 (dihydrochloride) | Pim |
| (3S,4S)-Tofacitinib | JAK |

TABLE 2-continued

Examples of kinase inhibitors and their targets.

| Kinase inhibitor | Target |
|---|---|
| (E)-AG 99 | EGFR |
| (E)-Necrosulfonamide | Mixed Lineage Kinase |
| [6]-Gingerol | AMPK; Apoptosis |
| 1,2,3,4,5,6-Hexabromocyclohexane | JAK |
| 1,3-Dicaffeoylquinic acid | Akt; PI3K |
| 1-Azakenpaullone | GSK-3 |
| 1-Naphthyl PP1 | Src |
| 1-NM-PP1 | PKD |
| 2,5-Dihydroxybenzoic acid | Endogenous Metabolite; FGFR |
| 2-D08 | c-RET, SUMO, TAM Receptor, IL Receptor, PI3K, VEGFR, GSK-3 |
| 2-Deoxy-D-glucose | Hexokinase |
| 2-Methoxy-1,4-naphthoquinone | PKC |
| 2-Phospho-L-ascorbic acid trisodium salt | c-Met/HGFR |
| 3,4-Dimethoxycinnamic acid | ROS |
| 3BDO | Autophagy; mTOR |
| 3-Bromopyruvic acid | Hexokinase |
| 3-Methyladenine (3-MA) | Autophagy, PI3K |
| 4μ8C | IRE1 |
| 5-Aminosalicylic Acid | NF-κB; PAK; PPAR |
| 5-Bromoindole | GSK-3 |
| 5-Iodotubercidin | Adenosine Kinase |
| 6-(Dimethylamino)purine | Serine/threonin kina |
| 6-Bromo-2-hydroxy-3-methoxybenzaldehyde | IRE1 |
| 7,8-Dihydroxyflavone | Trk Receptor |
| 7-Hydroxy-4-chromone | Src |
| 7-Methoxyisoflavone | AMPK |
| 8-Bromo-cAMP sodium salt | PKA |
| A 419259 (trihydrochloride) | Src |
| A 77-01 | TGF-β Receptor |
| A 83-01 sodium salt | TGF-β Receptor |
| A-443654 | Akt |
| A-484954 | CaMK |
| A66 | PI3K |
| A-674563 | Akt, CDK, PKA |
| A-769662 | AMPK |
| ABBV-744 | Epigenetic Reader Do |
| Abemaciclib | CDK |
| Abrocitinib | JAK |
| ABT-702 dihydrochloride | Adenosine Kinase |
| AC480 (BMS-599626) | EGFR, HER2 |
| AC710 | c-Kit; FLT3; PDGFR |
| Acalabrutinib (ACP-196) | BTK |
| Acalisib | PI3K |
| acalisib (GS-9820) | PI3K |
| ACHP (Hydrochloride) | IKK |
| ACTB-1003 | FGFR; VEGFR |
| Acumapimod | p38 MAPK |
| AD80 | c-RET, Src, S6 Kinase |
| Adavosertib | Wee1 |
| AEE788 | EGFR |
| Afatinib | Autophagy; EGFR |
| Afatinib (BIBW2992) | EGFR, HER2 |
| Afatinib (dimaleate) | Autophagy; EGFR |
| Afuresertib | Akt |
| AG 555 | EGFR |
| AG-1024 | IGF-1R |
| AG126 | ERK |
| AG-1478 | EGFR |
| AG-18 | EGFR |
| AG-490 | Autophagy; EGFR; STAT |
| Agerafenib | Raf |
| AGL-2263 | Insulin Receptor |
| AICAR | AMPK; Autophagy; Mitophagy |
| AIM-100 | Ack1 |
| AKT inhibitor VIII | Akt |
| AKT Kinase Inhibitor | Akt |
| Akt1 and Akt2-IN-1 | Akt |
| Akti-1/2 | Akt |
| Alectinib | ALK |
| Alisertib (MLN8237) | Aurora Kinase |
| ALK inhibitor 1 | ALK |
| ALK inhibitor 2 | ALK |
| ALK-IN-1 | ALK |

TABLE 2-continued

Examples of kinase inhibitors and their targets.

| Kinase inhibitor | Target |
| --- | --- |
| Allitinib tosylate | EGFR |
| Alofanib | FGFR |
| Alpelisib | PI3K |
| Altiratinib | c-Met/HGFR; FLT3; Trk Receptor; VEGFR |
| ALW-II-41-27 | Ephrin Receptor |
| AM-2394 | Glucokinase |
| Amcasertib (BBI503) | Stemness kinase |
| AMG 337 | c-Met |
| AMG 900 | Aurora Kinase |
| AMG 925 (HCl) | CDK; FLT3 |
| AMG-208 | c-Met/HGFR |
| AMG319 | PI3K |
| AMG-337 | c-Met/HGFR |
| AMG-3969 | Glucokinase |
| AMG-458 | c-Met |
| AMG-47a | Src |
| AMG-900 | Aurora Kinase |
| Amlexanox | Immunology & Inflammation related |
| Amuvatinib (MP-470) | c-Kit, FLT3, PDGFR |
| ANA-12 | Trk Receptor |
| Anacardic Acid | Histone Acetyltransferase |
| Anlotinib (AL3818) dihydrochloride | VEGFR |
| AP26113-analog (ALK-IN-1) | ALK, EGFR |
| Apatinib | VEGFR, c-RET |
| Apatinib?mesylate | VEGFR |
| Apigenin | P450 (e.g. CYP17) |
| Apitolisib | mTOR; PI3K |
| APS-2-79 | MEK |
| APY0201 | Interleukin Related; PIKfyve |
| APY29 | IRE1 |
| AR-A014418 | GSK-3 |
| ARN-3236 | Salt-inducible Kinase (SIK) |
| ARQ 531 | Btk |
| AS-252424 | PI3K |
| AS601245 | JNK |
| AS-604850 | PI3K |
| AS-605240 | Autophagy; PI3K |
| Asciminib | Bcr-Abl |
| Asciminib (ABL001) | Bcr-Abl |
| ASP3026 | ALK |
| ASP5878 | FGFR |
| AST 487 | Bcr-Abl; c-Kit; FLT3; VEGFR |
| AST-1306 | EGFR |
| Astragaloside IV | ERK; JNK; MMP |
| AT13148 | Akt, S6 Kinase, ROCK, PKA |
| AT7519 | CDK |
| AT7867 | Akt, S6 Kinase |
| AT9283 | Aurora Kinase, Bcr-Abl, JAK |
| Atuveciclib | CDK |
| Atuveciclib S-Enantiomer | CDK |
| Aurora A inhibitor I | Aurora Kinase |
| Autophinib | Autophagy, PI3K |
| AUZ 454 | CDK |
| AV-412 | EGFR |
| Avapritinib | c-Kit |
| Avitinib (maleate) | EGFR |
| AX-15836 | ERK |
| Axitinib | c-Kit, PDGFR, VEGFR |
| AZ 3146 | Kinesin |
| AZ 628 | Raf |
| AZ 960 | JAK |
| AZ1495 | IRAK |
| AZ191 | DYRK |
| AZ20 | ATM/ATR |
| AZ-23 | Trk Receptor |
| AZ304 | Raf |
| AZ31 | ATM/ATR |
| AZ3146 | Mps1 |
| AZ32 | ATM/ATR |
| AZ5104 | EGFR |
| AZ960 | JAK |
| Azaindole 1 | ROCK |
| AZD 6482 | Autophagy; PI3K |
| AZD0156 | ATM/ATR |
| AZD-0364 | ERK |
| AZD1080 | GSK-3 |

TABLE 2-continued

Examples of kinase inhibitors and their targets.

| Kinase inhibitor | Target |
| --- | --- |
| AZD1152 | Aurora Kinase |
| AZD1208 | Pim |
| AZD1390 | ATM/ATR |
| AZD-1480 | JAK |
| AZD2858 | GSK-3 |
| AZD2932 | PDGFR, VEGFR, FLT3, c-Kit |
| AZD3229 | c-Kit |
| AZD3264 | IκB/IKK |
| AZD3463 | ALK, IGF-1R |
| AZD-3463 | ALK; Autophagy; IGF-1R |
| AZD3759 | EGFR |
| AZD4547 | FGFR |
| AZD4573 | CDK |
| AZD5363 | Akt |
| AZD5438 | CDK |
| AZD-5438 | CDK |
| AZD6482 | PI3K |
| AZD6738 | ATM/ATR |
| AZD7507 | c-Fms |
| AZD7545 | PDHK |
| AZD7762 | Chk |
| AZD-7762 | Checkpoint Kinase (Chk) |
| AZD8055 | mTOR |
| AZD-8055 | Autophagy; mTOR |
| AZD8186 | PI3K |
| AZD8330 | MEK |
| AZD8835 | PI3K |
| AZD-8835 | PI3K |
| AZM475271 | Src |
| Bafetinib (INNO-406) | Bcr-Abl |
| Bakuchiol | Immunology & Inflammation related |
| Barasertib-HQPA | Aurora Kinase |
| Bardoxolone Methyl | IκB/IKK |
| Baricitinib | JAK |
| BAW2881 (NVP-BAW2881) | VEGFR, Raf, c-RET |
| BAY 11-7082 | E2 conjugating, IκB/IKK |
| Bay 11-7085 | IκB/IKK |
| BAY 1217389 | Kinesin, Serine/threonin kinase |
| BAY 1895344 (BAY-1895344) | ATM/ATR |
| Bay 65-1942 (hydrochloride) | IKK |
| BAY1125976 | Akt |
| BAY1217389 | Mps1 |
| BAY-1895344 (hydrochloride) | ATM/ATR |
| BAY-61-3606 | Syk |
| BDP5290 | ROCK |
| BEBT-908 | PI3K |
| Belizatinib | ALK; Trk Receptor |
| Bemcentinib | TAM Receptor |
| Bentamapimod | JNK |
| Berbamine (dihydrochloride) | Bcr-Abl |
| Berberine (chloride hydrate) | Autophagy; Bacterial; ROS; Topoisomerase |
| Berzosertib | ATM/ATR |
| BF738735 | PI4K |
| BFH772 | VEGFR |
| BGG463 | CDK |
| BGT226 (NVP-BGT226) | mTOR, PI3K |
| BI 2536 | PLK |
| BI-4464 | FAK; Ligand for Target Protein |
| BI605906 | IKK |
| BI-78D3 | JNK |
| BI-847325 | MEK, Aurora Kinase |
| BIBF 1202 | VEGFR |
| BIBF0775 | TGF-β Receptor |
| BI-D1870 | S6 Kinase |
| Bikinin | GSK-3 |
| Bimiralisib | mTOR; PI3K |
| Binimetinib | Autophagy; MEK |
| Binimetinib (MEK162, ARRY-162, ARRY-438162) | MEK |
| BIO | GSK-3 |
| BIO-acetoxime | GSK-3 |
| Biochanin A | FAAH |
| Bisindolyhnaleimide I | PKC |
| Bisindolylmaleimide I (GF109203X) | PKC |
| Bisindolylmaleimide IX (Ro 31-8220 Mesylate) | PKC |

TABLE 2-continued

Examples of kinase inhibitors and their targets.

| Kinase inhibitor | Target |
| --- | --- |
| BIX 02188 | MEK |
| BIX 02189 | MEK |
| BIX02188 | ERK; MEK |
| BIX02189 | ERK; MEK |
| BLU-554 (BLU554) | FGFR |
| BLU9931 | FGFR |
| BLZ945 | CSF-1R |
| BMS 777607 | c-Met/HGFR; TAM Receptor |
| BMS-265246 | CDK |
| BMS-345541 | IκB/IKK |
| BMS-5 | LIM Kinase (LIMK) |
| BMS-509744 | Itk |
| BMS-536924 | IGF-1R |
| BMS-582949 | p38 MAPK |
| BMS-690514 | EGFR; VEGFR |
| BMS-754807 | c-Met, IGF-1R, Trk receptor |
| BMS-777607 | TAM Receptor, c-Met |
| BMS-794833 | c-Met, VEGFR |
| BMS-911543 | JAK |
| BMS-935177 | BTK, Trk receptor, c-RET |
| BMS-986142 | Btk |
| BMS-986195 | Btk |
| BMX-IN-1 | BMX Kinase; Btk |
| BOS-172722 | Mps1 |
| Bosutinib (SKI-606) | Src |
| BPR1J-097 Hydrochloride | FLT3 |
| bpV (HOpic) | PTEN |
| BQR-695 | PI4K |
| B-Raf IN 1 | Raf |
| BRAF inhibitor | Raf |
| B-Raf inhibitor 1 | Raf |
| Brivanib | Autophagy; VEGFR |
| Brivanib (BMS-540215) | FGFR, VEGFR |
| Brivanib Alaninate (BMS-582664) | FGFR, VEGFR |
| BS-181 | CDK |
| BTK IN-1 | Btk |
| Btk inhibitor 1 | Btk |
| BTK inhibitor 1 (Compound 27) | BTK |
| Btk inhibitor 1 (R enantiomer) | Btk |
| Btk inhibitor 2 | Btk |
| Bucladesine (calcium salt) | PKA |
| Bucladesine (sodium salt) | PKA |
| Buparlisib | PI3K |
| Butein | EGFR |
| BX517 | PDK-1 |
| BX795 | PDK-1 |
| BX-795 | IκB/IKK, PDK |
| BX-912 | PDK |
| Ca2+ channel agonist 1 | Calcium Channel; CDK |
| CA-4948 | TLR, IL Receptor |
| Cabozantinib | c-Kit; c-Met/HGFR; FLT3; TAM Receptor; VEGFR |
| Cabozantinib (S-malate) | VEGFR |
| Cabozantinib (XL184, BMS-907351) | c-Met, VEGFR |
| Cabozantinib malate (XL184) | TAM Receptor, VEGFR |
| CAL-130 (Hydrochloride) | PI3K |
| CaMKII-IN-1 | CaMK |
| Canertinib (CI-1033) | EGFR, HER2 |
| Capivasertib | Akt; Autophagy |
| Capmatinib | c-Met/HGFR |
| Casein Kinase II Inhibitor IV | Casein Kinase |
| CAY10505 | PI3K |
| CC-115 | DNA-PK, mTOR |
| CC-223 | mTOR |
| CC-401 (hydrochloride) | JNK |
| CC-671 | CDK |
| CC-90003 | ERK |
| CCG215022 | PKA |
| CCT 137690 | Aurora Kinase |
| CCT020312 | Eukaryotic Initiation Factor (eIF); PERK |
| CCT128930 | Akt |
| CCT129202 | Aurora Kinase |
| CCT137690 | Aurora Kinase |
| CCT196969 | Raf, Src |
| CCT241533 (hydrochloride) | Checkpoint Kinase (Chk) |
| CCT241736 | Aurora Kinase; FLT3 |
| CCT245737 | Chk |

TABLE 2-continued

Examples of kinase inhibitors and their targets.

| Kinase inhibitor | Target |
| --- | --- |
| CCT-251921 | CDK |
| CDK9-IN-1 | CDK; HIV |
| CDK9-IN-2 | CDK |
| CDKI-73 | CDK |
| CDK-IN-2 | CDK |
| Cediranib | Autophagy; PDGFR; VEGFR |
| Cediranib Maleate | VEGFR |
| Centrinone | Polo-like Kinase (PLK) |
| Centrinone-B | Polo-like Kinase (PLK) |
| CEP-28122 (mesylate salt) | ALK |
| CEP-32496 | CSF-1R, Raf |
| CEP-33779 | JAK |
| CEP-37440 | ALK; FAK |
| CEP-40783 | c-Met/HGFR; TAM Receptor |
| Ceralasertib | ATM/ATR |
| Cerdulatinib | JAK; Syk |
| Cerdulatinib (PRT062070, PRT2070) | JAK |
| Ceritinib | ALK; IGF-1R; Insulin Receptor |
| Ceritinib dihydrochloride | ALK; IGF-1R; Insulin Receptor |
| CFI-400945 | PLK |
| CFI-402257 hydrochloride | Mps1 |
| cFMS Receptor Inhibitor II | c-Fms |
| c-Fms-IN-2 | c-Fms |
| CG-806 | Btk; FLT3 |
| CGI1746 | BTK |
| CGI-1746 | Autophagy; Btk |
| CGK733 | ATM/ATR |
| CGK733 | ATM/ATR |
| CGP 57380 | MNK |
| CGP60474 | PKC; VEGFR |
| CH5132799 | PI3K |
| CH5183284 | FGFR |
| CH5183284 (Debio-1347) | FGFR |
| CH7057288 | Trk Receptor |
| Chelerythrine Chloride | Autophagy; PKC |
| CHIR-124 | Chk |
| CHIR-98014 | GSK-3 |
| CHIR-99021 | Autophagy; GSK-3 |
| CHIR-99021 (CT99021) | GSK-3 |
| Chk2 Inhibitor II (BML-277) | Chk |
| Chloropyramine hydrochloride | FAK; Histamine Receptor; VEGFR |
| CHMFL-BMX-078 | BMX Kinase |
| CHR-6494 | Haspin Kinase |
| Chroman 1 | ROCK |
| Chrysophanic Acid | EGFR, mTOR |
| CHZ868 | JAK |
| CI-1040 | MEK |
| CID 2011756 | Serine/threonin kina |
| CID755673 | Serine/threonin kinase, CaMK |
| CK1-IN-1 | Casein Kinase |
| c-Kit-IN-1 | c-Kit; c-Met/HGFR |
| CL-387785 | EGFR |
| CL-387785 (EKI-785) | EGFR |
| CLK1-IN-1 | CDK |
| c-Met inhibitor 1 | c-Met/HGFR |
| CNX-2006 | EGFR |
| CNX-774 | Btk |
| Cobimetinib | MEK |
| Cobimetinib (GDC-0973, RG7420) | MEK |
| Cobimetinib (hemifumarate) | MEK |
| Cobimetinib (racemate) | MEK |
| Compound 401 | DNA-PK |
| Corynoxeine | ERK1/2 |
| CP21R7 | GSK-3 |
| CP21R7 (CP21) | Wnt/beta-catenin |
| CP-466722 | ATM/ATR |
| CP-673451 | PDGFR |
| CP-724714 | EGFR, HER2 |
| Crenolanib | Autophagy; FLT3; PDGFR |
| Crizotinib | ALK; Autophagy; c-Met/HGFR |
| CRT0066101 | Serine/threonin kinase, CaMK |
| CRT0066101 dihydrochloride | PKD |
| CT7001 hydrochloride | CDK |
| Cucurbitacin E | Autophagy; CDK |
| Cucurbitacin I | JAK; STAT |
| CUDC-101 | EGFR, HDAC, HER2 |

TABLE 2-continued

Examples of kinase inhibitors and their targets.

| Kinase inhibitor | Target |
| --- | --- |
| CUDC-907 | HDAC, PI3K |
| CVT-313 | CDK |
| CX-6258 | Pim |
| Cyasterone | EGFR |
| CYC065 | CDK |
| CYC116 | Aurora Kinase, VEGFR |
| CZ415 | mTOR |
| CZC24832 | PI3K |
| CZC-25146 | LRRK2 |
| CZC-54252 | LRRK2 |
| CZC-8004 | Bcr-Abl |
| D 4476 | Casein Kinase |
| D4476 | Autophagy; Casein Kinase |
| Dabrafenib | Raf |
| Dabrafenib (GSK2118436) | Raf |
| Dabrafenib (Mesylate) | Raf |
| Dabrafenib Mesylate | Raf |
| Dacomitinib | EGFR |
| Dacomitinib (PF299804, PF299) | EGFR |
| Dactolisib (Tosylate) | Autophagy; mTOR; PI3K |
| Danthron | AMPK |
| Danusertib | Aurora Kinase; Autophagy |
| Danusertib (PHA-739358) | Aurora Kinase, Bcr-Abl, c-RET, FGFR |
| Daphnetin | PKA, EGFR, PKC |
| Dasatinib | Bcr-Abl, c-Kit, Src |
| Dasatinib Monohydrate | Src, c-Kit, Bcr-Abl |
| DB07268 | JNK |
| DCC-2618 | c-Kit |
| DCP-LA | PKC |
| DDR1-IN-1 | Others |
| Decernotinib (VX-509) | JAK |
| Defactinib | FAK |
| Degrasyn | Autophagy; Bcr-Abl; Deubiquitinase |
| Deguelin | Akt, PI3K |
| Dehydrocorydaline (chloride) | p38 MAPK |
| Dehydrocostus Lactone | IκB/IKK |
| DEL-22379 | ERK |
| Delcasertib | PKC |
| Delgocitinib | JAK |
| Derazantinib | FGFR |
| Derazantinib(ARQ-087) | FGFR |
| Dicoumarol | PDHK |
| Dihexa | c-Met/HGFR |
| Dihydromyricetin | Autophagy; mTOR |
| Dilmapimod | p38 MAPK |
| Dinaciclib | CDK |
| Dinaciclib (SCH727965) | CDK |
| DMAT | Casein Kinase |
| DMH1 | TGF-beta/Smad |
| DMH-1 | Autophagy; TGF-b Receptor |
| Doramapimod | p38 MAPK; Raf |
| Doramapimod (BIRB 796) | p38 MAPK |
| Dorsomorphin (Compound C) | AMPK |
| Dorsomorphin (dihydrochloride) | AMPK; Autophagy; TGF-β Receptor |
| Dovitinib | c-Kit; FGFR; FLT3; PDGFR; VEGFR |
| Dovitinib (lactate) | FGFR |
| Dovitinib (TKI-258) Dilactic Acid | c-Kit, FGFR, FLT3, PDGFR, VEGFR |
| Dovitinib (TKI258) Lactate | FLT3, c-Kit, FGFR, PDGFR, VEGFR |
| Dovitinib (TKI-258, CHIR-258) | c-Kit, FGFR, FLT3, PDGFR, VEGFR |
| DPH | Bcr-Abl |
| Dubermatinib | TAM Receptor |
| Duvelisib | PI3K |
| Duvelisib (R enantiomer) | PI3K |
| EAI045 | EGFR |
| eCF506 | Src |
| Edicotinib | c-Fms |
| eFT-508 (eFT508) | MNK |
| EG00229 | VEGFR |
| EGFR-IN-3 | EGFR |
| Ellagic acid | Topoisomerase |
| EMD638683 | SGK |
| EMD638683 (R-Form) | SGK |
| EMD638683 (S-Form) | SGK |
| Emodin | Autophagy; Casein Kinase |
| Empesertib | Mps1 |
| Encorafenib | Raf |

TABLE 2-continued

Examples of kinase inhibitors and their targets.

| Kinase inhibitor | Target |
| --- | --- |
| ENMD-2076 | Aurora Kinase, FLT3, VEGFR |
| ENMD-2076 L-(+)-Tartaric acid | Aurora Kinase, FLT3, VEGFR |
| Entospletinib | Syk |
| Entospletinib (GS-9973) | Syk |
| Entrectinib | ALK; Autophagy; ROS; Trk Receptor |
| Entrectinib (RXDX-101) | Trk receptor, ALK |
| Enzastaurin | Autophagy; PKC |
| Enzastaurin (LY317615) | PKC |
| Erdafitinib | FGFR |
| Erdafitinib (JNJ-42756493) | FGFR |
| ERK5-IN-1 | ERK |
| Erlotinib | EGFR |
| ETC-1002 | AMPK; ATP Citrate Lyase |
| ETC-206 | MNK |
| ETP-46321 | PI3K |
| ETP-46464 | ATM/ATR, mTOR |
| Everolimus (RAD001) | mTOR |
| Evobrutinib | Btk |
| EX229 | AMPK |
| Falnidamol | EGFR |
| Fasudil (Hydrochloride) | Autophagy; PKA; ROCK |
| Fedratinib | JAK |
| Fenebrutinib | Btk |
| Ferulic acid | FGFR |
| Ferulic acid methyl ester | p38 MAPK |
| FGF401 | FGFR |
| FGFR4-IN-1 | FGFR |
| FIIN-2 | FGFR |
| FIIN-3 | EGFR; FGFR |
| Filgotinib | JAK |
| Filgotinib (GLPG0634) | JAK |
| Fimepinostat | HDAC; PI3K |
| Fingolimod | LPL Receptor; PAK |
| Fisogatinib | FGFR |
| Flavopiridol | Autophagy; CDK |
| FLLL32 | JAK |
| FLT3-IN-1 | FLT3 |
| FLT3-IN-2 | FLT3 |
| Flufenamic acid | AMPK; Calcium Channel; Chloride Channel; COX; Potassium Channel |
| Flumatinib | Bcr-Abl; c-Kit; PDGFR |
| Flumatinib (mesylate) | Bcr-Abl; c-Kit; PDGFR |
| FM381 | JAK |
| FM-381 | JAK |
| FMK | Ribosomal S6 Kinase (RSK) |
| FN-1501 | CDK; FLT3 |
| Foretinib | c-Met/HGFR; VEGFR |
| Foretinib (GSK1363089) | c-Met, VEGFR |
| Formononetin | Others |
| Fostamatinib (R788) | Syk |
| FR 180204 | ERK |
| FRAX1036 | PAK |
| FRAX486 | PAK |
| FRAX597 | PAK |
| Fruquintinib | VEGFRs |
| Futibatinib | FGFR |
| G-5555 | PAK |
| G-749 | FLT3 |
| Galunisertib | TGF-β Receptor |
| Gambogenic acid | Others |
| Gandotinib | FGFR; FLT3; JAK; VEGFR |
| Gandotinib (LY2784544) | JAK |
| GDC-0077 | PI3K |
| GDC-0084 | PI3K, mTOR |
| GDC-0326 | PI3K |
| GDC-0339 | Pim |
| GDC-0349 | mTOR |
| GDC-0575 (ARRY-575, RG7741) | Chk |
| GDC-0623 | MEK |
| GDC-0834 | Btk |
| GDC-0834 (Racemate) | Btk |
| GDC-0834 (S-enantiomer) | Btk |
| GDC-0879 | Raf |
| Gedatolisib (PF-05212384, PKI-587) | mTOR, PI3K |
| Gefitinib | Autophagy; EGFR |
| Gefitinib (ZD1839) | EGFR |

TABLE 2-continued

Examples of kinase inhibitors and their targets.

| Kinase inhibitor | Target |
| --- | --- |
| Genistein | EGFR, Topoisomerase |
| Gilteritinib (ASP2215) | FLT3, TAM Receptor |
| Ginkgolide C | AMPK; MMP; Sirtuin |
| Ginsenoside Rb1 | Autophagy; IRAK; Mitophagy; Na+/K+ ATPase; NF-κB |
| Ginsenoside Re | Amyloid-β; JNK; NF-κB |
| Glesatinib (hydrochloride) | c-Met/HGFR; TAM Receptor |
| GLPG0634 analog | JAK |
| GNE-0877 | LRRK2 |
| GNE-317 | PI3K |
| GNE-477 | mTOR; PI3K |
| GNE-493 | mTOR; PI3K |
| GNE-7915 | LRRK2 |
| GNE-9605 | LRRK2 |
| GNF-2 | Bcr-Abl |
| GNF-5 | Bcr-Abl |
| GNF-5837 | Trk Receptor |
| GNF-7 | Bcr-Abl |
| Gö 6983 | PKC |
| Gö6976 | FLT3, JAK, PKC |
| Golvatinib (E7050) | c-Met, VEGFR |
| GSK 3 Inhibitor IX | CDK; GSK-3 |
| GSK 650394 | SGK |
| GSK1059615 | mTOR, PI3K |
| GSK1070916 | Aurora Kinase |
| GSK180736A | ROCK |
| GSK180736A (GSK180736) | ROCK |
| GSK1838705A | ALK, IGF-1R |
| GSK1904529A | IGF-1R |
| GSK2110183 (hydrochloride) | Akt |
| GSK2256098 | FAK |
| GSK2292767 | PI3K |
| GSK2334470 | PDK |
| GSK2578215A | LRRK2 |
| GSK2606414 | PERK |
| GSK2636771 | PI3K |
| GSK2656157 | PERK |
| GSK269962A | ROCK |
| GSK2850163 | IRE1 |
| GSK2982772 | TNF-alpha, NF-κB |
| GSK-3 inhibitor 1 | GSK-3 |
| GSK429286A | ROCK |
| GSK461364 | PLK |
| GSK481 | TNF-alpha |
| GSK'481 | RIP kinase |
| GSK'547 | TNF-alpha |
| GSK583 | NF-κB |
| GSK650394 | Others |
| GSK690693 | Akt |
| GSK-872 | RIP kinase |
| GSK'963 | NF-κB, TNF-alpha |
| Gusacitinib | JAK; Syk |
| GW 441756 | Trk Receptor |
| GW 5074 | Raf |
| GW2580 | CSF-1R |
| GW441756 | Trk receptor |
| GW5074 | Raf |
| GW788388 | TGF-beta/Smad |
| GW843682X | Polo-like Kinase (PLK) |
| GZD824 | Bcr-Abl |
| GZD824 Dimesylate | Bcr-Abl |
| H3B-6527 | FGFR |
| H-89 (dihydrochloride) | Autophagy; PKA |
| HA-100 | Myosin; PKA; PKC |
| Harmine | 5-HT Receptor; DYRK; RAD51 |
| Harmine hydrochloride | DYRK |
| HER2-Inhibitor-1 | EGFR, HER2 |
| Hesperadin | Aurora Kinase |
| HG-10-102-01 | LRRK2 |
| HG-14-10-04 | ALK |
| HG6-64-1 | Raf |
| HG-9-91-01 | Salt-inducible Kinase (SIK) |
| Hispidulin | Pim |
| HMN-214 | PLK |
| Honokiol | Akt, MEK |
| HS-10296 hydrochloride | EGFR |

TABLE 2-continued

Examples of kinase inhibitors and their targets.

| Kinase inhibitor | Target |
| --- | --- |
| HS-1371 | Serine/threonin kina |
| HS-173 | PI3K |
| HTH-01-015 | AMPK |
| hVEGF-IN-1 | VEGFR |
| Hydroxyfasudil | ROCK |
| Ibrutinib | Btk |
| Ibrutinib (PCI-32765) | BTK |
| IC261 | Casein Kinase |
| IC-87114 | PI3K |
| Icotinib | EGFR |
| ID-8 | DYRK |
| Idelalisib | Autophagy; PI3K |
| Idelalisib (CAL-101, GS-1101) | PI3K |
| IITZ-01 | Autophagy; PI3K |
| IKK 16 | IKK; LRRK2 |
| IKK-IN-1 | IKK |
| Ilginatinib | JAK |
| IM-12 | GSK-3 |
| Imatinib | Autophagy; Bcr-Abl; c-Kit; PDGFR |
| Imatinib Mesylate (STI571) | Bcr-Abl, c-Kit, PDGFR |
| IMD 0354 | IκB/IKK |
| IMD-0354 | IKK |
| IMD-0560 | IKK |
| INCB053914 (phosphate) | Pim |
| Indirubin | GSK-3 |
| Indirubin-3'-monoxime | 5-Lipoxygenase; GSK-3 |
| Infigratinib | FGFR |
| Ingenol | PKC |
| INH14 | IKK |
| IPA-3 | PAK |
| Ipatasertib | Akt |
| IPI-3063 | PI3K |
| IPI549 | PI3K |
| IPI-549 | PI3K |
| IQ-1S (free acid) | JNK |
| IRAK inhibitor 1 | IRAK |
| IRAK inhibitor 2 | IRAK |
| IRAK inhibitor 4 (trans) | IRAK |
| IRAK inhibitor 6 | IRAK |
| IRAK-1-4 Inhibitor I | IRAK |
| IRAK4-IN-1 | IRAK |
| Irbinitinib (ARRY-380, ONT-380) | HER2 |
| ISCK03 | c-Kit |
| Isorhamnetin | MEK; PI3K |
| Isorhamnetin 3-O-neohesperoside | Others |
| Isovitexin | JNK; NF-κB |
| ISRIB (trans-isomer) | PERK |
| Itacitinib | JAK |
| ITD-1 | TGF-β Receptor |
| ITX5061 | p38 MAPK |
| JAK3-IN-1 | JAK |
| JANEX-1 | JAK |
| JH-II-127 | LRRK2 |
| JH-VIII-157-02 | ALK |
| JI-101 | Ephrin Receptor; PDGFR; VEGFR |
| JNJ-38877605 | c-Met |
| JNJ-38877618 | c-Met/HGFR |
| JNJ-47117096 hydrochloride | FLT3; MELK |
| JNJ-7706621 | Aurora Kinase, CDK |
| JNK Inhibitor IX | JNK |
| JNK-IN-7 | JNK |
| JNK-IN-8 | JNK |
| K02288 | TGF-beta/Smad |
| K03861 | CDK |
| K145 (hydrochloride) | SPHK |
| kb NB 142-70 | PKD |
| KD025 (SLx-2119) | ROCK |
| KDU691 | PI4K |
| Kenpaullone | CDK |
| Ki20227 | c-Fms |
| Ki8751 | c-Kit, PDGFR, VEGFR |
| kira6 | Others |
| KN-62 | CaMK |
| KN-92 (hydrochloride) | CaMK |
| KN-93 | CaMK |
| KN-93 Phosphate | CaMK |

TABLE 2-continued

Examples of kinase inhibitors and their targets.

| Kinase inhibitor | Target |
| --- | --- |
| KPT-9274 | NAMPT, PAK |
| KRN 633 | VEGFR |
| KU-0063794 | mTOR |
| KU-55933 | ATM/ATR; Autophagy |
| KU-57788 | CRISPR/Cas9; DNA-PK |
| KU-60019 | ATM/ATR |
| KW-2449 | Aurora Kinase, Bcr-Abl, FLT3 |
| KX1-004 | Src |
| KX2-391 | Src |
| L-779450 | Autophagy; Raf |
| Lapatinib | EGFR, HER2 |
| Larotrectinib (LOXO-101) sulfate | Trk receptor |
| Larotrectinib sulfate | Trk Receptor |
| Lazertinib | EGFR |
| Lazertinib (YH25448, GNS-1480) | EGFR |
| Lck Inhibitor | Src |
| Lck inhibitor 2 | Src |
| LDC000067 | CDK |
| LDC1267 | TAM Receptor |
| LDC4297 | CDK |
| LDN-193189 2HCl | TGF-beta/Smad |
| LDN-212854 | TGF-β Receptor |
| LDN-214117 | TGF-beta/Smad |
| Leflunomide | Dehydrogenase |
| Leniolisib | PI3K |
| Lenvatinib | VEGFR |
| Lerociclib dihydrochloride | CDK |
| LFM-A13 | BTK |
| Lifirafenib | EGFR; Raf |
| Linifanib | Autophagy; FLT3; PDGFR; VEGFR |
| Linsitinib | IGF-1R; Insulin Receptor |
| LJH685 | S6 Kinase |
| LJI308 | S6 Kinase |
| L-Leucine | mTOR |
| LM22A-4 | Trk Receptor |
| LM22B-10 | Akt; ERK; Trk Receptor |
| Longdaysin | Casein Kinase; ERK |
| Lonidamine | Hexokinase |
| Lorlatinib | ALK |
| Lorlatinib?(PF-6463922) | ALK |
| Losmapimod | Autophagy; p38 MAPK |
| Losmapimod (GW856553X) | p38 MAPK |
| Loureirin B | ERK; JNK; PAI-1; Potassium Channel |
| LRRK2 inhibitor 1 | LRRK2 |
| LRRK2-IN-1 | LRRK2 |
| LSKL, Inhibitor of Thrombospondin (TSP-1) | TGF-β Receptor |
| LTURM34 | DNA-PK |
| Lucitanib | FGFR; VEGFR |
| Lupeol | Immunology & Inflammation related |
| LX2343 | Amyloid-P; Autophagy; Beta-secretase; PI3K |
| LXH254 | Raf |
| LXS196 | PKC |
| LY2090314 | GSK-3 |
| LY2109761 | TGF-beta/Smad |
| LY2409881 | IκB/IKK |
| LY2584702 | S6 Kinase |
| LY2584702 Tosylate | S6 Kinase |
| LY2608204 | Glucokinase |
| LY2857785 | CDK |
| LY2874455 | FGFR, VEGFR |
| LY294002 | Autophagy, PI3K |
| LY3009120 | Raf |
| LY3023414 | mTOR, PI3K, DNA-PK |
| LY3177833 | CDK |
| LY3200882 | TGF-β Receptor |
| LY3214996 | ERK |
| LY3295668 | Aurora Kinase |
| LY364947 | TGF-beta/Smad |
| LY-364947 | TGF-β Receptor |
| LYN-1604 hydrochloride | ULK |
| Magnolin | ERK1 |
| Masitinib | c-Kit; PDGFR |
| MBQ-167 | CDK; Ras |
| MC180295 | CDK |
| MCB-613 | Src |

TABLE 2-continued

Examples of kinase inhibitors and their targets.

| Kinase inhibitor | Target |
| --- | --- |
| MEK inhibitor | MEK |
| MELK-8a (hydrochloride) | MELK |
| Merestinib | c-Met/HGFR |
| Mesalamine | IκB/IKK, Immunology & Inflammation related |
| Metadoxine | PKA |
| Metformin (hydrochloride) | AMPK; Autophagy; Mitophagy |
| Methylthiouracil | ERK; Interleukin Related; NF-κB; TNF Receptor |
| MGCD-265 analog | c-Met/HGFR; VEGFR |
| MHP | SPHK |
| MHY1485 | Autophagy; mTOR |
| Midostaurin | PKC |
| Milciclib (PHA-848125) | CDK |
| Miltefosine | Akt |
| Miransertib | Akt |
| Mirin | ATM/ATR |
| Mirk-IN-1 | DYRK |
| Mitoxantrone | PKC; Topoisomerase |
| MK 2206 (dihydrochloride) | Akt; Autophagy |
| MK-2461 | c-Met, FGFR, PDGFR |
| MK2-IN-1 (hydrochloride) | MAPKAPK2 (MK2) |
| MK-3903 | AMPK |
| MK-5108 | Aurora Kinase |
| MK-8033 | c-Met/HGFR |
| MK8722 | AMPK |
| MK-8745 | Aurora Kinase |
| MK-8776 (SCH 900776) | CDK, Chk |
| MKC3946 | IRE1 |
| MKC8866 | IRE1 |
| MKC9989 | IRE1 |
| ML167 | CDK |
| ML347 | TGF-beta/Smad, ALK |
| ML-7 HCl | Serine/threonin kinase |
| MLi-2 | LRRK2 |
| MLN0905 | PLK |
| MLN120B | IKK |
| MLN2480 | Raf |
| MLN8054 | Aurora Kinase |
| MNS | Src; Syk |
| MNS (3,4-Methylenedioxy-β-nitrostyrene, MDBN) | Tyrosinase, p97, Syk, Src |
| Momelotinib | Autophagy; JAK |
| Motesanib | c-Kit; VEGFR |
| MP7 | PDK-1 |
| MP-A08 | SPHK |
| MPI-0479605 | Kinesin |
| Mps1-IN-1 | Mps1 |
| Mps1-IN-2 | Mps1; Polo-like Kinase (PLK) |
| MRT67307 HCl | IκB/IKK |
| MRT68921 (hydrochloride) | ULK |
| MRX-2843 | FLT3 |
| MSC2530818 | CDK |
| MSDC 0160 | Insulin Receptor |
| mTOR inhibitor-3 | mTOR |
| MTX-211 | EGFR; PI3K |
| Mubritinib | EGFR |
| Mutated EGFR-IN-1 | EGFR |
| Myricetin | MEK |
| NAMI-A | FAK |
| Naquotinib(ASP8273) | EGFR |
| Narciclasine | ROCK |
| Nazartinib | EGFR |
| Nazartinib (EGF816, NVS-816) | EGFR |
| NCB-0846 | Wnt/beta-catenin |
| Nec-1s (7-Cl—O—Nec1) | TNF-alpha |
| Necrostatin-1 | Autophagy; RIP kinase |
| Necrosulfonamide | Others |
| Nedisertib | DNA-PK |
| Neflamapimod | p38 MAPK |
| Nemiralisib | PI3K |
| Neohesperidin dihydrochalcone | ROS |
| Neratinib (HKI-272) | EGFR, HER2 |
| NG 52 | CDK |
| NH125 | CaMK |
| Nilotinib | Autophagy; Bcr-Abl |
| Nilotinib (AMN-107) | Bcr-Abl |
| Ningetinib | c-Met/HGFR; TAM Receptor; VEGFR |

TABLE 2-continued

Examples of kinase inhibitors and their targets.

| Kinase inhibitor | Target |
| --- | --- |
| Nintedanib | FGFR; PDGFR; VEGFR |
| NMS-P937 (NMS1286937) | PLK |
| Nocodazole | Autophagy, Microtubule Associated |
| Norcantharidin | EGFR, c-Met |
| Notoginsenoside R1 | Others |
| NPS-1034 | c-Met, TAM Receptor |
| NQDI-1 | ASK |
| NSC 228155 | EGFR; Epigenetic Reader Domain; Histone Acetyltransferase |
| NSC 42834 | JAK |
| NSC12 | FGFR |
| NSC781406 | mTOR; PI3K |
| NT157 | IGF-1R |
| NU 7026 | DNA-PK |
| NU2058 | CDK |
| NU6027 | CDK |
| NU6300 | CDK |
| NU7026 | DNA-PK |
| NU7441 (KU-57788) | DNA-PK, PI3K |
| NVP-2 | CDK |
| NVP-ACC789 | PDGFR; VEGFR |
| NVP-ADW742 | IGF-1R |
| NVP-BAW2881 | VEGFR |
| NVP-BHG712 | Bcr-Abl, Ephrin receptor, Raf, Src |
| NVP-BHG712 isomer | Ephrin Receptor |
| NVP-BSK805 2HCl | JAK |
| NVP-BVU972 | c-Met |
| NVP-LCQ195 | CDK |
| NVP-TAE 226 | FAK; Pyk2 |
| NVP-TAE 684 | ALK |
| NVS-PAK1-1 | PAK |
| Oclacitinib (maleate) | JAK |
| Oglufanide | VEGFR |
| Olmutinib | EGFR |
| Omipalisib | mTOR; PI3K |
| Omtriptolide | ERK |
| ON123300 | CDK |
| ONO-4059 (GS-4059) hydrochloride | BTK |
| Orantinib (TSU-68, SU6668) | PDGFR |
| Oridonin | Akt |
| OSI-027 | mTOR |
| OSI-420 | EGFR |
| OSI-930 | c-Kit, CSF-1R, VEGFR |
| Osimertinib | EGFR |
| OSU-03012 (AR-12) | PDK |
| OTS514 hydrochloride | TOPK |
| OTS964 | TOPK |
| OTSSP167 (hydrochloride) | MELK |
| P276-00 | CDK |
| p38α inhibitor 1 | p38 MAPK |
| p38-α MAPK-IN-1 | p38 MAPK |
| Pacritinib | FLT3; JAK |
| Palbociclib (hydrochloride) | CDK |
| Palbociclib (isethionate) | CDK |
| Palomid 529 | mTOR |
| Palomid 529 (P529) | mTOR |
| Pamapimod | p38 MAPK |
| Parsaclisib | PI3K |
| Pazopanib | c-Kit, PDGFR, VEGFR |
| PCI 29732 | Btk |
| PCI-33380 | Btk |
| PD 169316 | Autophagy; p38 MAPK |
| PD0166285 | Wee1 |
| PD0325901 | MEK |
| PD153035 | EGFR |
| PD158780 | EGFR |
| PD-166866 | FGFR |
| PD168393 | EGFR |
| PD173074 | FGFR, VEGFR |
| PD173955 | Bcr-Abl |
| PD184352 (CI-1040) | MEK |
| PD318088 | MEK |
| PD98059 | MEK |
| Peficitinib | JAK |
| Pelitinib | EGFR; Src |
| Pelitinib (EKB-569) | EGFR |

TABLE 2-continued

Examples of kinase inhibitors and their targets.

| Kinase inhibitor | Target |
| --- | --- |
| Pemigatinib | FGFR |
| Perifosine (KRX-0401) | Akt |
| Pexidartinib | c-Fms; c-Kit |
| Pexmetinib (ARRY-614) | p38 MAPK, Tie-2 |
| PF-00562271 Besylate | FAK |
| PF-03814735 | Aurora Kinase; VEGFR |
| PF-04217903 | c-Met |
| PF-04217903 (methanesulfonate) | c-Met/HGFR |
| PF-04691502 | Akt, mTOR, PI3K |
| PF-04965842 | JAK |
| PF-05231023 | FGFR |
| PF-06273340 | Trk receptor |
| PF-06409577 | AMPK |
| PF-06447475 | LRRK2 |
| PF-06459988 | EGFR |
| PF06650833 | IRAK |
| PF-06651600 | JAK |
| PF-06700841 (P-Tosylate) | JAK |
| PF-3758309 | PAK |
| PF-431396 | FAK |
| PF-4708671 | S6 Kinase |
| PF-477736 | Chk |
| PF-4800567 | Casein Kinase |
| PF-4989216 | PI3K |
| PF-543 (Citrate) | SPHK |
| PF-562271 | FAK |
| PF-573228 | FAK |
| PFK15 | Autophagy |
| PFK158 | Autophagy |
| PH-797804 | p38 MAPK |
| PHA-665752 | c-Met |
| PHA-680632 | Aurora Kinase |
| PHA-767491 | CDK |
| PHA-793887 | CDK |
| Phenformin (hydrochloride) | AMPK |
| Phorbol 12-myristate 13-acetate | PKC; SPHK |
| PHT-427 | Akt, PDK |
| PI-103 | Autophagy, DNA-PK, mTOR, PI3K |
| PI-103 (Hydrochloride) | DNA-PK; mTOR; PI3K |
| PI-3065 | PI3K |
| PI3K-IN-1 | PI3K |
| PI3Kδ-IN-2 | PI3K |
| PI4KIII beta inhibitor 3 | PI4K |
| Piceatannol | Syk |
| Picfeltarraenin IA | AChE |
| Picropodophyllin | IGF-1R |
| Pictilisib (GDC-0941) | PI3K |
| PIK-293 | PI3K |
| PIK-294 | PI3K |
| PIK-75 | DNA-PK; PI3K |
| PIK-75 HCl | DNA-PK, PI3K |
| PIK-93 | PI3K |
| PIK-III | Autophagy, PI3K |
| Pilaralisib | PI3K |
| Pilaralisib analogue | PI3K |
| Pim1/AKK1-IN-1 | Pim |
| PIM-447 (dihydrochloride) | Pim |
| Pimasertib | MEK |
| Pitavastatin Calcium | HMG-CoA Reductase |
| PKC-IN-1 | PKC |
| PKC-theta inhibitor | PKC |
| PKM2 inhibitor(compound 3k) | PKM |
| Pluripotin | ERK; Ribosomal S6 Kinase (RSK) |
| PLX-4720 | Raf |
| PLX647 | c-Fms; c-Kit |
| PLX7904 | Raf |
| PLX8394 | Raf |
| PND-1186 | FAK |
| PND-1186 (VS-4718) | FAK |
| Poloxime | Polo-like Kinase (PLK) |
| Poloxin | Polo-like Kinase (PLK) |
| Ponatinib (AP24534) | Bcr-Abl, FGFR, PDGFR, VEGFR |
| Poziotinib (HM781-36B) | HER2, EGFR |
| PP1 | Src |
| PP121 | DNA-PK, mTOR, PDGFR, Src, VEGFR, Bcr-Abl |
| PP2 | Src |

TABLE 2-continued

Examples of kinase inhibitors and their targets.

| Kinase inhibitor | Target |
| --- | --- |
| PQ 401 | IGF-1R |
| PQR620 | mTOR |
| Prexasertib | Checkpoint Kinase (Chk) |
| PRN1008 | Btk |
| PRN1371 | FGFR |
| PRN694 | Itk |
| PROTAC CDK9 Degrader-1 | CDK; PROTAC |
| Protein kinase inhibitors 1 hydrochloride | DYRK |
| PRT-060318 | Syk |
| PRT062607 (Hydrochloride) | Syk |
| PS-1145 | IκB/IKK |
| Psoralidin | Estrogen/progestogen Receptor |
| Purvalanol A | CDK |
| Purvalanol B | CDK |
| PYR-41 | E1 Activating |
| Pyridone 6 | JAK |
| Pyrotinib dimaleate | EGFR |
| Quercetin | Src, Sirtuin, PKC, PI3K |
| Quizartinib (AC220) | FLT3 |
| R112 | Syk |
| R1487 (Hydrochloride) | p38 MAPK |
| R1530 | VEGFR |
| R-268712 | TGF-β Receptor |
| R406 | FLT3, Syk |
| R406 (free base) | Syk |
| R547 | CDK |
| R788 (Fostamatinib) Disodium | Syk |
| Rabusertib (LY2603618) | Chk |
| Radotinib | Bcr-Abl |
| RAF265 | Autophagy; Raf; VEGFR |
| RAF265 (CHIR-265) | Raf, VEGFR |
| RAF709 | Raf |
| Ralimetinib (LY2228820) | p38 MAPK |
| Rapamycin (Sirolimus) | Autophagy, mTOR |
| Ravoxertinib | ERK |
| Rebastinib | Bcr-Abl; FLT3; Src |
| Refametinib | MEK |
| Refametinib (RDEA119, Bay 86-9766) | MEK |
| Regorafenib | Autophagy; PDGFR; Raf; VEGFR |
| Repotrectinib | ALK; ROS; Trk Receptor |
| RepSox | TGF-beta/Smad |
| Resveratrol | Autophagy; IKK; Mitophagy; Sirtuin |
| Reversine | Adenosine Receptor, Aurora Kinase |
| RG13022 | EGFR |
| RG14620 | EGFR |
| RGB-286638 (free base) | CDK; GSK-3; JAK; MEK |
| Ribociclib | CDK |
| Ridaforolimus (Deforolimus, MK-8669) | mTOR |
| Rigoscrtib (ON-01910) | PLK |
| Rigosertib (sodium) | Polo-like Kinase (PLK) |
| Rimacalib | CaMK |
| RIP2 kinase inhibitor 1 | RIP kinase |
| RIP2 kinase inhibitor 2 | RIP kinase |
| RIPA-56 | RIP kinase |
| Ripasudil | ROCK |
| Ripretinib | c-Kit; PDGFR |
| RK-24466 | Src |
| RKI-1447 | ROCK |
| RN486 | Btk |
| Ro 28-1675 | Glucokinase |
| Ro 5126766 | MEK; Raf |
| Ro3280 | PLK |
| Ro-3306 | CDK |
| RO4987655 | MEK |
| RO9021 | Svk |
| Roblitinib | FGFR |
| Rociletinib | EGFR |
| Rociletinib (CO-1686, AVL-301) | EGFR |
| Rociletinib hydrobromide | EGFR |
| Rogaratinib | FGFR |
| Roscovitine (Seliciclib, CYC202) | CDK |
| Rosmarinic acid | IκB/IKK |
| Ruboxistaurin (LY333531 HCl) | PKC |
| Ruxolitinib | Autophagy; JAK; Mitophagy |

TABLE 2-continued

Examples of kinase inhibitors and their targets.

| Kinase inhibitor | Target |
| --- | --- |
| Ruxolitinib (phosphate) | Autophagy; JAK; Mitophagy |
| Ruxolitinib (S enantiomer) | Autophagy; JAK |
| RXDX-106 (CEP-40783) | TAM Receptor |
| S49076 | c-Met, FGFR, TAM Receptor |
| SAFit2 | Akt |
| Salidroside | mTOR |
| Salubrinal | PERK |
| Sapanisertib | Autophagy; mTOR |
| Sapitinib | EGFR |
| SAR-020106 | Chk |
| SAR125844 | c-Met |
| SAR131675 | VEGFR |
| SAR-20347 | JAK |
| SAR-260301 | PI3K |
| SAR405 | Autophagy; PI3K |
| SAR407899 | ROCK |
| Saracatinib | Autophagy; Src |
| Saracatinib (AZD0530) | Src |
| Savolitinib | c-Met/HGFR |
| Savolitinib(AZD6094, HMPL-504) | c-Met |
| SB 202190 | Autophagy; p38 MAPK |
| SB 203580 | Autophagy; Mitophagy; p38 MAPK |
| SB 203580 (hydrochloride) | Autophagy; Mitophagy; p38 MAPK |
| SB 239063 | p38 MAPK |
| SB 242235 | p38 MAPK |
| SB 415286 | GSK-3 |
| SB 525334 | TGF-β Receptor |
| SB1317 | CDK; FLT3; JAK |
| SB202190 (FHPI) | p38 MAPK |
| SB203580 | p38 MAPK |
| SB216763 | GSK-3 |
| SB239063 | p38 MAPK |
| SB415286 | GSK-3 |
| SB431542 | TGF-beta/Smad |
| SB-431542 | TGF-β Receptor |
| SB505124 | TGF-beta/Smad |
| SB-505124 | TGF-β Receptor |
| SB525334 | TGF-beta/Smad |
| SB590885 | Raf |
| SB-590885 | Raf |
| SBE 13 HCl | PLK |
| SBI-0206965 | Autophagy |
| SC-514 | IκB/IKK |
| SC66 | Akt |
| SC79 | Akt |
| SCH-1473759 (hydrochloride) | Aurora Kinase |
| SCH772984 | ERK |
| SCH900776 | Checkpoint Kinase (Chk) |
| Schisandrin B (Sch B) | ATM/ATR, P-gp |
| Scopoletin | Immunology & Inflammation related |
| SCR-1481B1 | c-Met/HGFR; VEGFR |
| Scutellarein | Autophagy; Src |
| Scuteliarin | Akt; STAT |
| SD 0006 | p38 MAPK |
| SD-208 | TGF-beta/Smad |
| SEL120-34A (monohydrochloride) | CDK |
| Seletalisib | PI3K |
| Seletalisib (UCB-5857) | PI3K |
| Seliciclib | CDK |
| Selitrectinib | Trk Receptor |
| Selonsertib (GS-4997) | ASK |
| Selumetinib | MEK |
| Selumetinib (AZD6244) | MEK |
| Semaxanib (SU5416) | VEGFR |
| Semaxinib | VEGFR |
| Senexin A | CDK |
| Sennoside B | PDGFR |
| Serabelisib | PI3K |
| Serabelisib (INK-1117, MLN-1117, TAK-117) | PI3K |
| SF1670 | PTEN |
| SF2523 | PI3K, DNA-PK, Epigenetic Reader Domain, mTOR |
| SGI-1776 | Autophagy; Pim |
| SGI-1776 free base | Pim |
| SGI-7079 | VEGFR |
| SGX-523 | c-Met |

TABLE 2-continued

Examples of kinase inhibitors and their targets.

| Kinase inhibitor | Target |
| --- | --- |
| Silmitasertib | Autophagy; Casein Kinase |
| Simurosertib | CDK |
| Sitravatinib | c-Kit; Discoidin Domain Receptor; FLT3; Trk Receptor; VEGFR |
| Sitravatinib (MGCD516) | Ephrin receptor, c-Kit, TAM Receptor, VEGFR, Trk receptor |
| SJ000291942 | TGF-β Receptor |
| SK1-IN-1 | SPHK |
| Skatole | Aryl Hydrocarbon Receptor; p38 MAPK |
| Skepinone-L | p38 MAPK |
| SKF-86002 | p38 MAPK |
| SKI II | S1P Receptor |
| SKLB1002 | VEGFR |
| SKLB4771 | FLT3 |
| SL327 | MEK |
| SL-327 | MEK |
| SLV-2436 | MNK |
| SLx-2119 | ROCK |
| SM 16 | TGF-β Receptor |
| SMI-16a | Pim |
| SMI-4a | Pim |
| SNS-032 | CDK |
| SNS-032 (BMS-387032) | CDK |
| SNS-314 | Aurora Kinase |
| SNS-314 Mesylate | Aurora Kinase |
| Sodium dichloroacetate (DCA) | Dehydrogenase |
| Sodium Monofluorophosphate | phosphatase |
| Solanesol (Nonaisoprenol) | FAK |
| Solcitinib | JAK |
| Sorafenib | Raf |
| Sorafenib Tosylate | PDGFR, Raf, VEGFR |
| Sotrastaurin | PKC |
| SP600125 | JNK |
| Spebrutinib | Btk |
| SPHINX31 | Serine/threonin kina |
| SR-3029 | Casein Kinase |
| SR-3306 | JNK |
| SR-3677 | Autophagy; ROCK |
| Src Inhibitor 1 | Src |
| SRPIN340 | SRPK |
| S-Ruxolitinib (INCB018424) | JAK |
| SSR128129E | FGFR |
| Staurosporine | PKA; PKC |
| STF-083010 | IRE1 |
| STO-609 | CaMK |
| SU 5402 | FGFR; PDGFR; VEGFR |
| SU11274 | c-Met |
| SU14813 | c-Kit; PDGFR; VEGFR |
| SU14813 (maleate) | c-Kit; PDGFR; VEGFR |
| SU1498 | VEGFR |
| SU5402 | FGFR, VEGFR |
| SU5408 | VEGFR |
| SU6656 | Src |
| SU9516 | CDK |
| Sulfatinib | FGFR; VEGFR |
| SUN11602 | FGFR |
| Sunitinib | PDGFR, c-Kit, VEGFR |
| Sunitinib Malate | c-Kit, PDGFR, VEGFR |
| T56-LIMKi | LIM Kinase (LIMK) |
| TA-01 | Casein Kinase; p38 MAPK |
| TA-02 | p38 MAPK |
| TAE226 (NVP-TAE226) | FAK |
| TAE684 (NVP-TAE684) | ALK |
| TAK-285 | EGFR, HER2 |
| TAK-580 | Raf |
| TAK-593 | PDGFR; VEGFR |
| TAK-632 | Raf |
| TAK-659 | Syk, FLT3 |
| TAK-715 | p38 MAPK |
| TAK-733 | MEK |
| TAK-901 | Aurora Kinase |
| TAK-960 | Polo-like Kinase (PLK) |
| Takinib | IL Receptor |
| Talmapimod | p38 MAPK |
| Tandutinib | FLT3 |
| Tandutinib (MLN518) | FLT3 |

TABLE 2-continued

Examples of kinase inhibitors and their targets.

| Kinase inhibitor | Target |
| --- | --- |
| Tanzisertib | JNK |
| Tanzisertib(CC-930) | JNK |
| tarloxotinib bromide | EGFR |
| TAS-115 mesylate | c-Met/HGFR; VEGFR |
| TAS-301 | PKC |
| TAS6417 | EGFR |
| Taselisib | PI3K |
| Tat-NR2B9c | p38 MAPK |
| Tat-NR2B9C (TFA) | p38 MAPK |
| Tauroursodeoxycholate (Sodium) | Caspase; ERK |
| Tauroursodeoxycholate dihydrate | Caspase; ERK |
| Taxifolin (Dihydroquercetin) | VEGFR |
| TBB | Casein Kinase |
| TBK1/IKKε-IN-2 | IKK |
| TC13172 | Mixed Lineage Kinase |
| TC-DAPK 6 | DAPK |
| TCS 359 | FLT3 |
| TCS JNK 5a | JNK |
| TCS PIM-11 | Pim |
| TCS-PIM-1-4a | Pim |
| TDZD-8 | GSK-3 |
| Telatinib | c-Kit, PDGFR, VEGFR |
| Temsirolimus (CCI-779, NSC 683864) | mTOR |
| Tenalisib | PI3K |
| Tenalisib (RP6530) | PI3K |
| Tepotinib | Autophagy; c-Met/HGFR |
| Tepotinib (EMD 1214063) | c-Met |
| TG 100572 (Hydrochloride) | FGFR; PDGFR; Src; VEGFR |
| TG003 | CDK |
| TG100-115 | PI3K |
| TG100713 | PI3K |
| TG101209 | c-RET, FLT3, JAK |
| TGX-221 | PI3K |
| Theliatinib (HMPL-309) | EGFR |
| Thiazovivin | ROCK |
| THZ1 | CDK |
| THZ1-R | CDK |
| THZ2 | CDK |
| THZ531 | CDK |
| TIC10 | Akt |
| TIC10 Analogue | Akt |
| Tideglusib | GSK-3 |
| Tie2 kinase inhibitor | Tie-2 |
| Tirabrutinib | Btk |
| Tirbanibulin (Mesylate) | Microtubule/Tubulin; Src |
| Tivantinib | c-Met/HGFR |
| Tivantinib (ARQ 197) | c-Met |
| Tivozanib | VEGFR |
| Tivozanib (AV-951) | c-Kit, PDGFR, VEGFR |
| Toceranib phosphate | PDGFRP |
| Tofacitinib | JAK |
| Tofacitinib (CP-690550, Tasocitinib) | JAK |
| Tolimidone | Src |
| Tomivosertib | MNK |
| Torin 1 | Autophagy, mTOR |
| Torin 2 | ATM/ATR, mTOR |
| Torkinib | Autophagy; Mitophagy; mTOR |
| Tozasertib (VX-680, MK-0457) | Aurora Kinase |
| TP0427736 HCl | ALK |
| TP-0903 | TAM Receptor |
| TP-3654 | Pim |
| TPCA-1 | IκB/IKK |
| TPPB | PKC |
| TPX-0005 | Src, ALK |
| Trametinib | MEK |
| trans-Zeatin | ERK; MEK |
| Trapidil | PDGFR |
| Triciribine | Akt |
| TTP 22 | Casein Kinase |
| Tucatinib | EGFR |
| TWS119 | GSK-3 |
| TyK2-IN-2 | JAK |
| Tyk2-IN-4 | JAK |
| Tyrosine kinase inhibitor | c-Met/HGFR |
| Tyrosine kinase-IN-1 | FGFR; PDGFR; VEGFR |
| Tyrphostin 23 | EGFR |

TABLE 2-continued

Examples of kinase inhibitors and their targets.

| Kinase inhibitor | Target |
| --- | --- |
| Tyrphostin 9 | PDGFR, EGFR |
| Tyrphostin A9 | VEGFR |
| Tyrphostin AG 1296 | c-Kit, PDGFR |
| Tyrphostin AG 528 | EGFR |
| Tyrphostin AG 879 | HER2 |
| U0126 | Autophagy; MEK; Mitophagy |
| U0126-EtOH | MEK |
| UCB9608 | PI4K |
| UK-371804 HCl | Serine Protease |
| Ulixertinib | ERK |
| ULK-101 | ULK |
| UM-164 | Src, p38 MAPK |
| Umbralisib | PI3K |
| Umbralisib R-enantiomer | PI3K |
| UNC2025 | TAM Receptor, FLT3 |
| UNC2881 | TAM Receptor |
| Upadacitinib | JAK |
| Uprosertib | Akt |
| URMC-099 | LRRK2 |
| Vactosertib | TGF-β Receptor |
| Vactosertib (Hydrochloride) | TGF-β Receptor |
| Valrubicin | PKC |
| Vandetanib | Autophagy; VEGFR |
| Varlitinib | EGFR |
| Vatalanib (PTK787) 2HCl | VEGFR |
| VE-821 | ATM/ATR |
| VE-822 | ATM/ATR |
| Vecabrutinib | Btk; Itk |
| Vemurafenib | Autophagy; Raf |
| VER-246608 | PDHK |
| Verbascoside | Immunology & Inflammation related |
| Vistusertib | Autophagy; mTOR |
| Volasertib (BI 6727) | PLK |
| VO-Ohpic trihydrate | PTEN |
| Voxtalisib | mTOR; PI3K |
| VPS34 inhibitor 1 (Compound 19, PIK-III analogue) | PI3K |
| Vps34-IN-1 | PI3K |
| Vps34-IN-2 | PI3K |
| Vps34-PIK-III | Autophagy; PI3K |
| VS-5584 | mTOR; PI3K |
| VS-5584 (SB2343) | PI3K |
| VTX-27 | PKC |
| VX-11e | ERK |
| VX-702 | p38 MAPK |
| VX-745 | p38 MAPK |
| WAY-600 | mTOR |
| Wedelolactone | NF-κB |
| WEHI-345 | RIP kinase |
| WH-4-023 | Src |
| WHI-P154 | EGFR; JAK |
| WHI-P180 | EGFR; VEGFR |
| WHI-P97 | JAK |
| WNK463 | Serine/threonin kinase |
| Wogonin | CDK, Transferase |
| Wortmannin | ATM/ATR; DNA-PK; PI3K; Polo-like Kinase (PLK) |
| WP1066 | JAK; STAT |
| WYE-125132 (WYE-132) | mTOR |
| WYE-132 | mTOR |
| WYE-354 | mTOR |
| WZ3146 | EGFR |
| WZ-3146 | EGFR |
| WZ4002 | EGFR |
| WZ4003 | AMPK |
| WZ8040 | EGFR |
| X-376 | ALK; c-Met/HGFR |
| XL019 | JAK |
| XL147 analogue | PI3K |
| XL228 | Aurora Kinase; Bcr-Abl; IGF-1R; Src |
| XL388 | mTOR |
| XL413 (BMS-863233) | CDK |
| XMD16-5 | ACK |
| XMD17-109 | ERK |
| XMD8-87 | ACK |
| XMD8-92 | ERK |
| Y15 | FAK |

TABLE 2-continued

Examples of kinase inhibitors and their targets.

| Kinase inhibitor | Target |
| --- | --- |
| Y-27632 | ROCK |
| Y-33075 | ROCK |
| Y-39983 HCl | ROCK |
| YKL-05-099 | Salt-inducible Kinase (SIK) |
| YLF-466D | AMPK |
| YM-201636 | Autophagy; PI3K; PIKfyve |
| YU238259 | DNA-PK |
| Zanubrutinib | Btk |
| ZD-4190 | EGFR; VEGFR |
| ZINC00881524 | ROCK |
| ZINC00881524 (ROCK inhibitor) | ROCK |
| ZLN024 (hydrochloride) | AMPK |
| ZM 306416 | VEGFR |
| ZM 323881 HCl | VEGFR |
| ZM 336372 | Raf |
| ZM 39923 HCl | JAK |
| ZM 447439 | Aurora Kinase |
| ZM39923 (hydrochloride) | JAK |
| ZM-447439 | Aurora Kinase |
| Zotarolimus(ABT-578) | mTOR |
| ZSTK474 | PI3K |

REFERENCES

[1] Brook, M., C. R. Tchen, T. Santalucia, J. McIlrath, J. S. Arthur, J. Saklatvala and A. R. Clark (2006). "Posttranslational regulation of tristetraprolin subcellular localization and protein stability by p38 mitogen-activated protein kinase and extracellular signal-regulated kinase pathways." Mol Cell Biol 26(6): 2408-2418.

[2] Hitti, E., T. Iakovleva, M. Brook, S. Deppenmeier, A. D. Gruber, D. Radzioch, A. R. Clark, P. J. Blackshear, A. Kotlyarov and M. Gaestel (2006). "Mitogen-activated protein kinase-activated protein kinase 2 regulates tumor necrosis factor mRNA stability and translation mainly by altering tristetraprolin expression, stability, and binding to adenine/uridine-rich element." Mol Cell Biol 26(6): 2399-2407.

[3] Vlasova-St Louis, I. and P. R. Bohjanen (2016). "Feedback Regulation of Kinase Signaling Pathways by AREs and GREs." Cells 5(1): 4.

[4] Cao H, Lin R (2008). "Phosphorylation of recombinant tristetraprolin in vitro." Protein J. 27:163-9.

[5] Mahmoud, L., W. Moghrabi, K. S. A. Khabar and E. G. Hitti (2019). "Bi-phased regulation of the post-transcriptional inflammatory response by Tristetraprolin levels." RNA Biol 16(3): 309-319.

The features of the present invention disclosed in the specification, the claims, and/or in the accompanying figures may, both separately and in any combination thereof, be material for realizing the invention in various forms thereof.

The invention claimed is:

1. A method of determining if a patient is likely to respond to a cancer treatment with a targeted therapy compound selected from protein kinase inhibitors, small molecule inhibitors, and monoclonal antibody-based compounds, wherein the method comprises the following steps:
   i) providing a tumor sample of a patient, wherein said tumor sample comprises cancerous tissue and/or cancerous cells,
   ii) determining a level of phosphorylated tristetraprolin (TTP) in said tumor sample, and
   iii) comparing the level of phosphorylated TTP determined in step ii) to a control, wherein an increased level of phosphorylated TTP in said tumor sample compared to said control indicates that said patient is likely to respond to the cancer treatment using the targeted therapy compound.

2. The method according to claim 1, wherein said method further comprises:
   providing a tumor sample of said patient, and treating said tumor sample with one or more targeted therapy compound(s),
   determining a level of phosphorylated TTP in said treated tumor sample, and,
   comparing the level of phosphorylated TTP determined in said treated tumor sample to the level of phosphorylated TTP determined in step ii),
   wherein a decreased level of phosphorylated TTP in said treated tumor sample compared to the level of phosphorylated TTP determined in step ii) indicates that said patient is likely to respond to a treatment with said one or more targeted therapy compound(s).

3. The method according to claim 1, wherein said determining of a level of phosphorylated TTP is performed using an antibody or antigen-binding fragment thereof targeting phosphorylated TTP and/or TTP.

4. The method according to claim 1, wherein step ii) further comprises determining a cancer-related genetic variation in said tumor sample.

5. The method, according to claim 4, wherein the cancer-related genetic variation in said tumor is a KRAS mutation and/or an EGFR mutation.

6. A method of treatment of cancer in a patient, wherein said cancer is characterized by an increased level of phosphorylated TTP in cancer cells compared to non-cancerous cells, wherein said method comprises administering an effective dose of a targeted therapy compound selected from protein kinase inhibitors, small molecule inhibitors, and monoclonal antibody-based compounds to a patient in need thereof having said cancer.

7. The method according to claim 6, wherein said method comprises the steps of:
   a) obtaining a tumor sample, and optionally a non-tumor control sample, from the patient,
   b) determining the level of phosphorylated TTP in said tumor sample, and optionally in said non-tumor control sample,
   c) administering a therapeutically effective amount of said targeted therapy compound, if there is an increased level of phosphorylated TTP in the tumor sample compared to a control, which is optionally the non-tumor control sample of said patient, as determined in step b).

8. The method according to claim 6, wherein said targeted therapy compound is selected from BI-3406, lapitinib, AZ628, sorafenib2, TAK-6323, regorafenib4, CEP-32496, cabozantinib, and polo-like kinase inhibitors including PCM-075, volasertib, BI 2536, rigosertib (ON 01910), HMN-214, GSK461364, Ro3280, NMS-P937, TAK-960, cyclapolin 1, DAP-81, ZK-thiazolidinone, compound 36 (imidazopyridine derivative), LFM-A13, poloxin (thymoquinone derivative), poloxipan, purpurogallin (benzotropolone-containing compound), MLN0905, and SBE13.

9. The method, according to claim 8, wherein said targeted therapy compound is selected from volasertib and lapitinib.

10. The method according to claim 6, wherein said targeted therapy compound is co-administered with a chemotherapeutic agent, and/or with a therapeutic monoclonal antibody or antigen-binding fragment thereof, and/or with a checkpoint inhibitor, and/or with an interferon selected from Type-I IFN, Type-II IFN and Type-III IFN, and/or with a cytokine inhibitor, and/or with a small molecule drug.

11. The method, according to claim 10, wherein said targeted therapy compound is co-administered with a CTLA-4, PD-1, and/or PD-L1 targeting agent.

12. The method according to claim 6, wherein the level of phosphorylated TTP is reduced by administering said targeted therapy compound.

13. The method according to claim 6, wherein the method further comprises monitoring a treatment response, comprising the following steps:
   i) obtaining a sample from said patient of a first time point and a second time point,
   ii) determining a level of phosphorylated TTP in said first sample of said first time point and in said second sample of said second time point,
   iii) comparing the level determined in said first sample to the level determined in said second sample, wherein a decrease in the level determined in the second sample compared to the level determined in the first sample indicates that said targeted therapy compound is effective in treating said cancer.

* * * * *

SEQUENCE LISTING

```
<160> NUMBER OF SEQ ID NOS: 1

<210> SEQ ID NO 1
<211> LENGTH: 326
<212> TYPE: PRT
<213> ORGANISM: Homo sapiens
<220> FEATURE:
<221> NAME/KEY: MISC_FEATURE
<222> LOCATION: (1)..(326)
<223> OTHER INFORMATION: TTP Sequence

<400> SEQUENCE: 1

Met Asp Leu Thr Ala Ile Tyr Glu Ser Leu Leu Ser Leu Ser Pro Asp
1               5                   10                  15

Val Pro Val Pro Ser Asp His Gly Gly Thr Glu Ser Ser Pro Gly Trp
                20                  25                  30

Gly Ser Ser Gly Pro Trp Ser Leu Ser Pro Ser Asp Ser Ser Pro Ser
            35                  40                  45

Gly Val Thr Ser Arg Leu Pro Gly Arg Ser Thr Ser Leu Val Glu Gly
        50                  55                  60

Arg Ser Cys Gly Trp Val Pro Pro Pro Gly Phe Ala Pro Leu Ala
65                  70                  75                  80
```

```
Pro Arg Leu Gly Pro Glu Leu Ser Pro Ser Pro Thr Ser Pro Thr Ala
                85                  90                  95

Thr Ser Thr Thr Pro Ser Arg Tyr Lys Thr Glu Leu Cys Arg Thr Phe
            100                 105                 110

Ser Glu Ser Gly Arg Cys Arg Tyr Gly Ala Lys Cys Gln Phe Ala His
        115                 120                 125

Gly Leu Gly Glu Leu Arg Gln Ala Asn Arg His Pro Lys Tyr Lys Thr
    130                 135                 140

Glu Leu Cys His Lys Phe Tyr Leu Gln Gly Arg Cys Pro Tyr Gly Ser
145                 150                 155                 160

Arg Cys His Phe Ile His Asn Pro Ser Glu Asp Leu Ala Ala Pro Gly
                165                 170                 175

His Pro Pro Val Leu Arg Gln Ser Ile Ser Phe Ser Gly Leu Pro Ser
            180                 185                 190

Gly Arg Arg Thr Ser Pro Pro Pro Gly Leu Ala Gly Pro Ser Leu
        195                 200                 205

Ser Ser Ser Ser Phe Ser Pro Ser Ser Ser Pro Pro Pro Pro Gly Asp
    210                 215                 220

Leu Pro Leu Ser Pro Ser Ala Phe Ser Ala Ala Pro Gly Thr Pro Leu
225                 230                 235                 240

Ala Arg Arg Asp Pro Thr Pro Val Cys Cys Pro Ser Cys Arg Arg Ala
                245                 250                 255

Thr Pro Ile Ser Val Trp Gly Pro Leu Gly Gly Leu Val Arg Thr Pro
            260                 265                 270

Ser Val Gln Ser Leu Gly Ser Asp Pro Asp Glu Tyr Ala Ser Ser Gly
        275                 280                 285

Ser Ser Leu Gly Gly Ser Asp Ser Pro Val Phe Glu Ala Gly Val Phe
    290                 295                 300

Ala Pro Pro Gln Pro Val Ala Ala Pro Arg Arg Leu Pro Ile Phe Asn
305                 310                 315                 320

Arg Ile Ser Val Ser Glu
                325
```